US007659069B2

(12) United States Patent
Belyaev et al.

(10) Patent No.: US 7,659,069 B2
(45) Date of Patent: Feb. 9, 2010

(54) BINARY SIGNALING ASSAY USING A SPLIT-POLYMERASE

(75) Inventors: Alexander Belyaev, San Diego, CA (US); Craig Robert Monell, La Jolla, CA (US); Joseph A. Sorge, Wilson, WY (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/897,892

(22) Filed: Aug. 31, 2007

(65) Prior Publication Data

US 2009/0061426 A1    Mar. 5, 2009

(51) Int. Cl.
*C12Q 1/68* (2006.01)
(52) U.S. Cl. .......................................... 435/6; 435/91.2
(58) Field of Classification Search ........................ None
See application file for complete search history.

(56) References Cited

U.S. PATENT DOCUMENTS 5,985,548 A    11/1999  Collier et al.
6,511,809 B2    1/2003  Baez et al.

FOREIGN PATENT DOCUMENTS

WO    WO2006037064    *   4/2006
WO    WO02006074217   *   7/2006

OTHER PUBLICATIONS

Gullberg et al. (PNAS, 2004, vol. 101, No. 22, p. 8420-8424).*
Kelman et al. (Journal of Biological Chemistry, 1999, vol. 274, No. 40, p. 28751-28761).*
Platinum Taq (Invitrogen Catalog #10966-018/026).*
Josefsson et al. (Journal of Clinical Microbiology, 1999, vol. 37, No. 3, p. 490-496).*
Liu et al. (Biotechniques, 2002, 33(1):129-138).*
H.-T. Zhang, et al., "Protein Quantification from Complex Protein Mixtures Using a Proteomics Methodology with Single-Cell Resolution", Proc.Natl.Acad.Sci USA 2001 vol. 98(10), pp. 5497-5502.
T.C. Chang and S.H. Huang, "A Modified Immuno-Polymerase Chain Reaction for the Detection of Beta-Glucuronidase from *Escherichia coli*", J. Immunol. Methods 1997 vol. 208(1), pp. 35-42.
C.M. Niemeyer, et al., "Self-assembly of DNA-streptavidin Nanostructures and Their Use as Reagents in Immuno-PCR", Nucl. Acids.Res. 1999 vol. 27(23), pp. 4553-4561.
C.M. Niemeyer, et al., "Immuno-PCR: High Sensitivity Detection of Proteins by Nucleic Acid Amplification", Trends in Biotechnology 2005 vol. 23(4), pp, 208-216.
PCT International Search Report received in Application No. PCT/US2008/069975, dated Dec. 31, 2008, pp. 1-13.

* cited by examiner

*Primary Examiner*—Gary Benzion
*Assistant Examiner*—Stephanie K Mummert

(57) ABSTRACT

The present invention provides methods, kits and compositions for the detection of an analyte. In the methods of the invention, a complex is formed between two or more analyte specific probes (ASP) and an analyte. The analyte specific probes each have a portion of a polymerase which interact to form a functional polymerase complex upon binding of the ASP to the analyte. The functional polymerase complex then generates a detectable signal which is indicative of the presence and/or amount of the analyte in the sample.

21 Claims, 4 Drawing Sheets

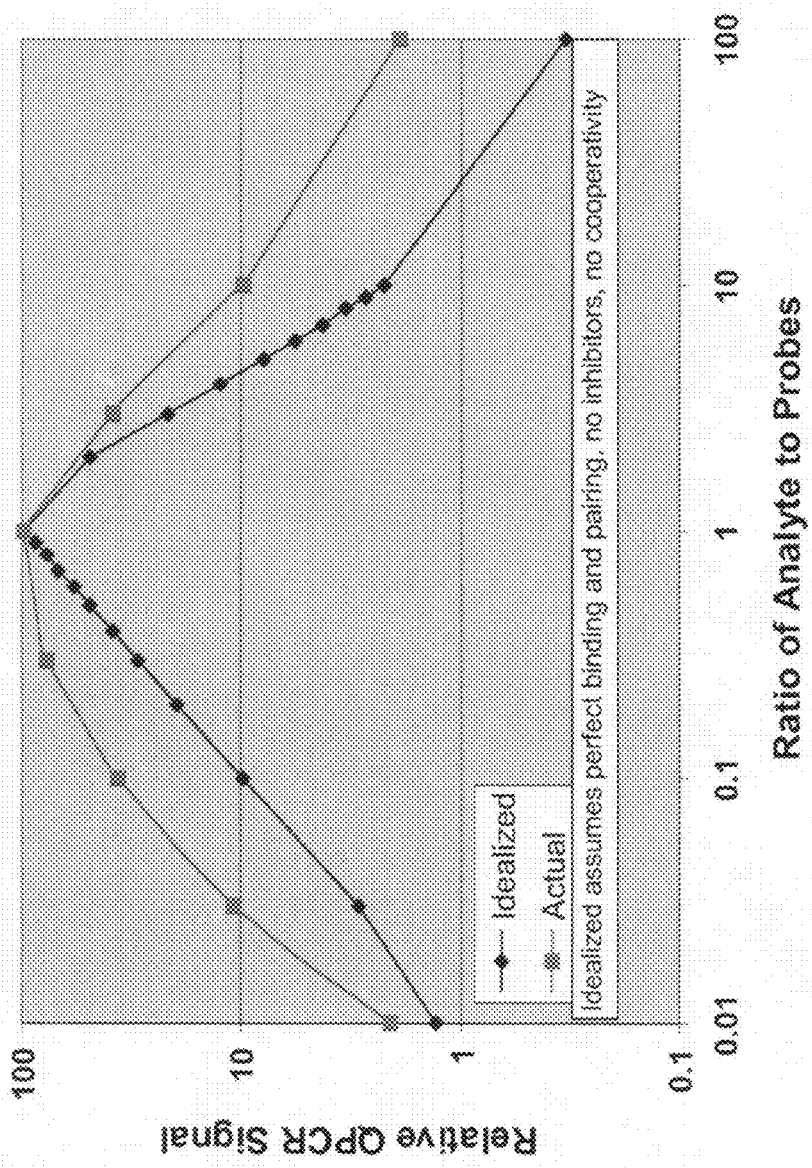

BINARY SIGNALING ASSAY USING A SPLIT-POLYMERASE

BACKGROUND

The development of immunoassays and advances in nucleic acid detection have advanced the art of the detection of biological samples. Several so called "immuno-PCR assays" are known in the art and combine aspects of an ELISA assay with PCR. The assays produce a detectable signal when the probes/antibodies bind an analyte in a sample allowing for the amplification of a target nucleic acid. Such assays are described in U.S. Publication No. 2002/0132233, U.S. Pat. No. 5,985,548, U.S. Publication No. 2005/0026161 and U.S. Publication No. 2005/0239108.

SUMMARY OF THE INVENTION

The present invention provides methods, kits and compositions for the detection of an analyte. In the methods of the invention, a complex is formed between two or more analyte specific probes (ASP) and an analyte. The analyte specific probes each have a portion of a polymerase which interact to form a functional polymerase complex upon binding of the ASP to the analyte. The functional polymerase complex then generates a detectable signal which is indicative of the presence and/or amount of the analyte in the sample.

In a first aspect, the invention is directed to a method of detecting an analyte. The method utilizes a reaction mixture which includes a first analyte specific probe, second analyte specific probe, polynucleotide template, first primer complementary to the polynucleotide template, Pfu polymerase, second primer complementary to an amplified template and an analyte. The first ASP includes a first binding moiety and a first portion of the klenow fragment of E. coli DNA polymerase I (klenow), and the second ASP includes a second binding moiety and a second portion of klenow. The first and second portions of klenow form a functional klenow complex when they interact with one another. The polynucleotide template includes one or more deoxyuracil and/or 2' O-methyl modifications.

The reaction mixture is incubated under conditions so as to permit binding of the binding moieties of the first and second ASPs to the analyte. When the first and second ASPs bind the analyte in close proximity to one another the first and second portions of klenow are able to interact, forming a functional klenow complex. The functional klenow complex may then extend the first primer, which is annealed to the polynucleotide template, so as to form an amplified template. Next, the amplified template is detected by annealing the second primer to the amplified template and extending the second primer with the Pfu polymerase so as to produce a detectable signal. The detection of the amplified template is indicative of the presence or amount of the analyte in the sample.

In a second aspect, the invention is directed to another method of detecting an analyte. The method entails contacting a sample with a reaction mixture so as to permit binding of a first ASP and a second ASP to an analyte, annealing of a first primer to a polynucleotide template and extension of the first primer. The first ASP includes a first binding moiety and a first portion of a first polymerase, and the second ASP includes a second binding moiety and a second portion of a first polymerase. When the first and second ASPs bind the analyte in close proximity to one another the first and second portions of the first polymerase are able to interact, forming a functional polymerase complex. The functional polymerase complex may then extend the first primer, which is annealed to the polynucleotide template, so as to form an amplified template. Next, the amplified template is detected by annealing a second primer to the amplified template and extending the second primer with a second polymerase so as to produce a detectable signal. The detection of the amplified template is indicative of the presence and/or amount of the analyte in the sample.

In yet another aspect, the invention is directed to a composition. In this embodiment the composition includes a first analyte specific probe, second analyte specific probe, polynucleotide template, first primer complementary to the polynucleotide template, second polymerase and a second primer complementary to an amplified template. The first ASP includes a binding moiety and a first portion of a first polymerase and the second ASP includes a binding moiety and a second portion of a first polymerase. The first and second portions of the first polymerase form a functional polymerase complex when they associate with one another.

In yet another aspect, the invention is directed to a composition. In this embodiment the composition includes a first analyte specific probe, second analyte specific probe and a second polymerase. The first ASP includes a binding moiety and a first portion of a first polymerase and the second ASP includes a binding moiety and a second portion of a first polymerase. The first and second portions of the first polymerase form a functional klenow complex when they associate with one another.

In yet another aspect, the invention is directed to a composition comprising a klenow fragment, wherein said klenow fragment has synthetic activity and consists of an amino acid sequence which is 95% or more identical to amino acids 201-605 of SEQ ID NO:1.

In other aspects, the invention is directed to kits containing the compositions of the invention and instructions for use.

BRIEF DESCRIPTION OF THE DRAWINGS

FIG. 4 depicts a dose response curve of varying concentrations of antibody in the presence of a constant amount of the N2 and C2 fragments of klenow.

DETAILED DESCRIPTION

Definitions

Figure 1:
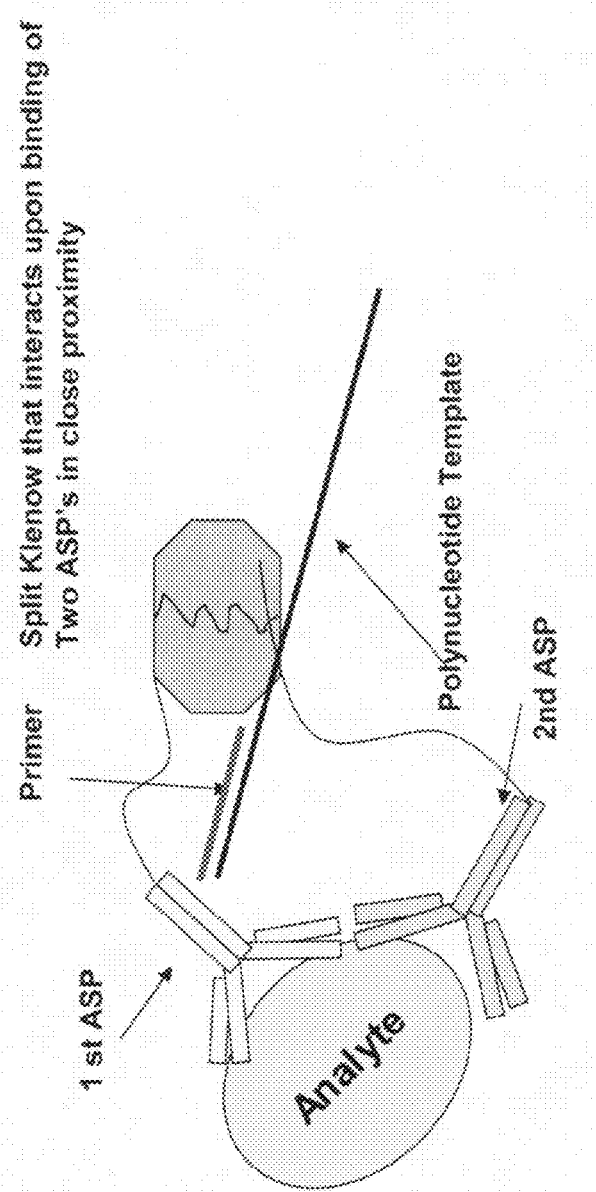
FIG. 1 illustrates one embodiment of the invention utilizing a first antibody coupled to a first portion of klenow and a second antibody coupled to a second portion of klenow.

As used herein the term "analyte" refers to a substance to be detected or assayed by the method of the present invention. Typical analytes may include, but are not limited to proteins, peptides, cell surface receptor, receptor ligand, nucleic acids, molecules, cells, microorganisms and fragments thereof, or any substance for which a binding moiety, e.g., antibodies, can be developed.

As used herein the term "binding moiety" refers to a molecule which stably binds an analyte. Binding moieties include, but are not limited to, a monoclonal antibody, polyclonal antibody, aptamer, cell surface receptor, receptor ligand, biotin, streptavidin, avidin, protein A and protein G and binding fragments thereof, e.g., Fab. The binding moiety is directly or indirectly coupled to a reactive molecule.

As used herein the terms "analyte specific probe" or "ASP", refers to a molecule having a binding moiety and a reactive moiety (e.g., a first or second portion of a polymerase). The binding moiety is operatively coupled to the reactive moiety. The analyte specific probes require that two or more probes bind in close proximity to one another in order for the reactive moieties to effectively interact. The analyte specific probes are in close proximity to one another when the two probes bind to their respective binding sites on the analyte and their active moieties interact.

As used herein, the term "interact", as applied to the reactive moieties of the ASPs, refers to bringing two or more reactive moieties (e.g., first and second portion of a polymerase) within close proximity to one another so as to allow the reactive moieties to physically associate. For example, when a pair of analyte specific probes having a first and second portion of a polymerase bind to an analyte, the first and second portions of the polymerase are brought into close proximity so as to interact and form a functional polymerase complex. This functional polymerase complex will then extend the 3' end of a primer hybridized to a polynucleotide template so as to form an amplification template. When the first and second portions of the polymerase are separated (do not interact) the portions substantially lack synthetic activity.

As used herein, the term "substantially lacking synthetic activity" refers to a first or second portion of a polymerase that has no more than 50%, 40%, 30%, 20% or 10% and preferably less than 1% of the synthetic activity of a functional polymerase complex.

As used herein, the term "portion" with reference to a first polymerase refers to a fragment of a nucleic acid polymerase that substantially lacks nucleic acid synthetic activity when isolated, but which has nucleic acid synthetic activity when it interacts with a second portion of the nucleic acid polymerase. As used herein a "portion" with respect to a first polymerase refers to fragments of 50-1000 amino acids, but which are less than the full-length polymerase. In one embodiment, the portion has at least 50, 60, 70 80, 90, 100, 150, 200, 250, 300, 350, 400, 450, 500, 550, or 600 or more amino acids of a nucleic acid polymerase, but less than the full-length polymerase. For example, a first portion of klenow can have the amino acid sequence of SEQ ID NO: 2, a second portion of the klenow can have the amino acid sequence of SEQ ID NO:3, while the full-length klenow comprises the amino acid sequence of SEQ ID NO:1.

As used herein, the term "functional polymerase complex" refers to two or more portions of a polymerase, as defined herein, which interact to form a polypeptide complex having synthetic activity (polymerase activity) that is at least 2× the synthetic activity of either portion alone (e.g., not in complex).

In a preferred embodiment, the binding moiety of the ASP is an antibody.

As used herein, the term "antibody" refers to an immunoglobulin protein which is capable of binding an antigen, e.g., analyte. Antibody includes any portion of an antibody that retains the ability to bind to the epitope recognized by the full length antibody, generally termed "epitope-binding fragments." Examples of antibody fragments preferably include, but are not limited to, Fab, Fab', and F(ab')$_2$, Fd, single-chain Fvs (scFv), single-chain antibodies, disulfide-linked Fvs (sdFv) and fragments comprising either a $V_L$ or $V_H$ domain. Epitope-binding fragments, including single-chain antibodies, may comprise the variable region(s) alone or in combination with the entirety or a portion of the following: hinge region, $C_H1$, $C_H2$, and $C_H3$ domains.

As used herein, "nucleic acid polymerase" or "polymerase" refers to an enzyme that catalyzes the polymerization of nucleotides. Generally, the enzyme will initiate synthesis at the 3'-end of the primer annealed to a nucleic acid template sequence, and will proceed toward the 5' end of the template strand. "DNA polymerase" catalyzes the polymerization of deoxyribonucleotides. Known DNA polymerases include, for example, *Pyrococcus furiosus* (Pfu) DNA polymerase (Lundberg et al., 1991, Gene, 108:1), *E. coli* DNA polymerase I (Lecomte and Doubleday, 1983, Nucleic Acids Res. 11:7505), T7 DNA polymerase (Nordstrom et al., 1981, J. Biol. Chem. 256:3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475: 32), *Thermococcus litoralis* (Tli) DNA polymerase (also referred to as Vent DNA polymerase, Cariello et al., 1991, Nucleic Acids Res, 19: 4193), 9°Nm DNA polymerase (discontinued product from New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteriol, 127: 1550), *Pyrococcus kodakaraensis* KOD DNA polymerase (Takagi et al., 1997, Appl. Environ. Microbiol. 63:4504), JDF-3 DNA polymerase (Patent application WO 0132887), *Pyrococcus* GB-D (PGB-D) DNA polymerase (Juncosa-Ginesta et al., 1994, Biotechniques, 16:820), T4 DNA polymerase and klenow. The polymerase activity of any of the above enzyme can be determined by methods well known in the art. In one embodiment, the method utilizes a first nucleic acid polymerase that is capable of amplifying a modified polynucleotide template and a second nucleic acid polymerase that is incapable of amplifying a modified polynucleotide template. Polymerases capable of amplifying a modified polynucleotide template and polymerases that are incapable of amplifying a polynucleotide template are known in the art and described herein. The invention utilizes a first polymerase that is split into a first and second portion. In a preferred embodiment, the first polymerase is a family A polymerase. In a more preferred embodiment, the polymerase that is split into a first and second portion is klenow.

As used herein, "coupled" refers to the association of two molecules though covalently and non-covalent interactions, e.g., by hydrogen, ionic, or Van-der-Waals bonds. Such bonds may be formed between at least two of the same or different atoms or ions as a result of redistribution of electron densities of those atoms or ions. For example, an enzyme may be coupled to an antibody as an antibody-enzyme fusion protein, via binding through a streptavidin-biotin interaction or through binding via an Fc protein A/G interaction (e.g., polymerase is coupled to protein A/G which in turn binds the Fc region of the antibody).

As used herein, a "fusion polypeptide" refers to a polypeptide comprising two or more polypeptides that are linked in frame to each other. As used herein, the term "linked" or "fused" means the linking together of two or more segments of a polypeptide or nucleic acid to form a fusion molecule that encodes two or more polypeptides linked in frame to each other. The two or more polypeptides may be linked directly or via a linker.

As used herein, the term "oligonucleotide" or "polynucleotide" refers polydeoxyribonucleotides (containing 2-deoxy-D-ribose), to polyribonucleotides (containing D-ribose) and to any polynucleotide which is an N-glycoside of a purine or pyrimidine base, or modified purine or pyrimidine base. An oligonucleotide may hybridize to other oligonucleotide or may self-hybridize, e.g., hairpin structure. An oligonucleotide includes, without limitation, single- and double-stranded oligonucleotides.

As used herein, the term "polynucleotide template" refers to nucleic acid sequence to which a primer hybridizes and which is replicated by a nucleic acid polymerase, e.g., in a PCR or primer extension reaction. In a preferred embodiment, the polynucleotide template is replicated when a first and second portion of a first polymerase interact so as to form a functional polymerase complex. As used herein, an "amplified template" is a nucleic acid sequence which was previously amplified by a polymerase, anneals to a primer and is copied in a second amplification reaction.

As used herein, "a modified polynucleotide template" refers to a polynucleotide template with one or more non-natural nucleotides that prevents the template from being copied by a first polymerase (e.g., Pfu polymerase) but not by a second polymerase (e.g., klenow or T4 polymerase). Such non-natural modifications include replacing thymine with a uracil and replacing 2' hydroxyls with 2'-O-methyl. Other suitable modifications may include 3' to 5' reversed deoxyribonucleotides (Qiang Liu et al. Biotechniques. 33:129-138 (July 2002)), hypoxanthine and other non-traditional nucleotides known in the art and described herein. A "modified nucleic acid template" can not be copied, (e.g., amplified) by a Pfu polymerase (*Pyrococcus furiosus* (Pfu) DNA polymerase (Lundberg et al., 1991, Gene, 108:1)), under the reaction conditions described herein (e.g., 1× Pfu buffer at 60-72° C.). Assays for determining whether a template is a modified polynucleotide template are described herein and known in the art.

As used herein, the term "complementary" refers to the concept of sequence complementarity between regions of two polynucleotide/oligonucleotide strands. It is known that an adenine base of a first polynucleotide region is capable of forming specific hydrogen bonds ("base pairing") with a base of a second polynucleotide region which is antiparallel to the first region if the base is thymine or uracil. Similarly, it is known that a cytosine base of a first polynucleotide strand is capable of base pairing with a base of a second polynucleotide strand which is antiparallel to the first strand if the base is guanine. A first region of a polynucleotide is complementary to a second region a different polynucleotide if, when the two regions are arranged in an antiparallel fashion, at least one nucleotide of the first region is capable of base pairing with a base of the second region. Therefore, it is not required for two complementary polynucleotides to base pair at every nucleotide position. "Complementary" can refer to a first polynucleotide that is 100% or "fully" complementary to a second polynucleotide and thus forms a base pair at every nucleotide position. "Complementary" also can refer to a first polynucleotide that is not 100% complementary (e.g., 90%, 80%, 70%, 60% complementary) contains mismatched nucleotides at one or more nucleotide positions.

As used herein, the terms "hybridization" or "annealing" is used to describe the pairing of complementary (including partially complementary) polynucleotide/oligonucleotide strands, e.g., primer and template. Hybridization and the strength of hybridization (i.e., the strength of the association between polynucleotide strands) is impacted by many factors well known in the art including the degree of complementarity between the polynucleotides, stringency of the conditions involved, the melting temperature ($T_m$) of the formed hybrid, the presence of other components (e.g., the presence or absence of polyethylene glycol), the molarity of the hybridizing strands, and the G:C content of the polynucleotide strands.

As used herein, when one polynucleotide is said to "hybridize" or "anneal" to another polynucleotide, it means that there is some complementarity between the two polynucleotides or that the two polynucleotides form a hybrid under high stringency conditions. When one polynucleotide is said to not hybridize to another polynucleotide, it means that there is no sequence complementarity between the two polynucleotides or that no hybrid forms between the two polynucleotides at a high stringency condition.

The term "nuclease" refers to an enzyme that possesses 5' to 3' endonuclease activity and/or 5' to 3' exonuclease activity (5' exonuclease). Enzymes possessing 5' endonucleolytic activity include DNA polymerase, e.g. DNA polymerase I from *E. coli*, and DNA polymerase from *Thermus aquaticus* (Taq), *Thermus thermophilus* (Tth), *Pyrococcus furiosus* (Pfu) and *Thermus flavus* (Tfl). The term "nuclease" also embodies FEN nucleases. FEN enzymes cleave 5' nucleic acid flaps. FEN nuclease enzymes include FEN enzymes derived from *Archaeglobus fulgidus, Methanococcus jannaschii, Pyrococcus furiosus*, human, mouse or *Xenopus laevis*. A nuclease according to the invention also includes *Saccharomyces cerevisiae* RAD27, and *Schizosaccharomyces pombe* RAD2, Pol I DNA polymerase associated 5' to 3' exonuclease domain, (e.g. *E. coli, Thermus aquaticus* (Taq), *Thermus flavus* (Tfl), *Bacillus caldotenax* (Bca), *Streptococcus pneumoniae*) and phage functional homologs of FEN including but not limited to T5 5' to 3' exonuclease, T7 gene 6 exonuclease and T3 gene 6 exonuclease.

As used herein, "cleavage reaction" refers to enzymatically separating an oligonucleotide (i.e. not physically linked to other fragments or nucleic acids by phosphodiester bonds) into fragments or nucleotides and fragments that are released from the oligonucleotide. A cleavage reaction is performed by an exonuclease activity, endonuclease activity or restriction enzyme activity. Cleavage reactions utilizing an endonuclease activity include the INVADER detection assay (Third Wave Technologies; Madison, Wis.) which is described in U.S. Pat. No. 6,348,314 and is herein incorporated by reference in their entirety. Cleavage reaction assays encompassed by the present methods also include MOLECULAR BEACON detection assays (supplied by a variety of commercial sources) and TAQMAN detection assays (supplied by a variety of commercial sources including Roche) which are described in U.S. Pat. Nos. 5,723,591; 5,925,517 and 5,804,375, each of which is herein incorporated by reference in its entirety. Cleavage reactions useful in the present invention are also described in U.S. Pat. No. 6,548,250 which is herein incorporated by reference.

As used herein, the term "cleavage product" is an oligonucleotide fragment that has been cleaved and released into solution in a cleavage reaction by a nuclease.

As used herein, the term "amplification", when applied to a nucleic acid sequence, refers to a process whereby one or more copies of a particular nucleic acid sequence is generated from a template nucleic acid. Generally amplification is carried out using a polymerase chain reaction (PCR) or ligase chain reaction (LCR), technologies well known in the art (Dieffenbach, C. W. and G. S. Dveksler (1995) *PCR Primer, a Laboratory Manual*, Cold Spring Harbor Press, Plainview, N.Y.). However, as used herein, amplification is also meant to include a single step replication/copying of a nucleic acid sequence (e.g., primer extension reaction).

The present invention provides methods, kits and compositions for the detection of an analyte. In the methods of the invention, a complex is formed between two or more analyte specific probes (ASP) and an analyte. The analyte specific probes each have a portion of a polymerase which interact to form a functional polymerase complex upon binding of the ASPs to the analyte. The functional polymerase complex generates a detectable signal which is indicative of the presence and/or amount of the analyte in the sample.

In a first aspect, the invention is directed to a method of detecting an analyte. The method utilizes a reaction mixture which includes a first analyte specific probe, second analyte specific probe, polynucleotide template, first primer complementary to the polynucleotide template, Pfu polymerase, second primer complementary to an amplified template and an analyte. Suitable analytes include, but are not limited to, proteins, oligonucleotides, cell surface receptors and receptor ligands. The first ASP includes a first binding moiety and a first portion of klenow, and the second ASP includes a second binding moiety and a second portion of klenow. The first and second portions of klenow form a functional klenow complex when they interact with one another. In one embodiment, the first portion of the first polymerase has the amino acid sequence of SEQ ID NO: 2 and the second portion of the first polymerase has the amino acid sequence of SEQ ID NO: 3. The binding moiety can be a monoclonal or polyclonal antibody, lectin, cell surface receptor, receptor ligand, peptide, carbohydrate, aptamer, biotin, streptavidin, avidin, protein A or protein G. The polynucleotide template includes one or more deoxyuracil and/or 2' O-methyl modifications.

The reaction mixture is incubated under conditions so as to permit binding of the binding moieties of the first and second ASPs to the analyte. When the first and second ASPs bind the analyte in close proximity to one another the first and second portions of klenow are able to interact, forming a functional klenow complex. The functional klenow complex may then extend the first primer, which is annealed to the polynucleotide template, so as to form an amplified template. Next, the amplified template is detected by annealing the second primer to the amplified template and extending the second primer with the Pfu polymerase so as to produce a detectable signal. The detection of the amplified template is indicative of the presence and/or amount of the analyte in the sample.

In a second aspect, the invention is directed to another method of detecting an analyte. The method entails contacting a sample with a reaction mixture so as to permit binding of a first ASP and a second ASP to an analyte, annealing of a first primer to a polynucleotide template and extension of the first primer. The first ASP includes a first binding moiety and a first portion of a first polymerase, and the second ASP includes a second binding moiety and a second portion of a first polymerase. When the first and second ASPs bind the analyte in close proximity to one another the first and second portions of the first polymerase are able to interact, forming a functional polymerase complex. The functional polymerase complex may then extend the first primer, which is annealed to the polynucleotide template, so as to form an amplified template. Next, the amplified template is detected by annealing a second primer to the amplified template and extending the second primer with a second polymerase so as to produce a detectable signal. The detection of the amplified template is indicative of the presence and/or amount of the analyte in the sample.

In any of the above aspects of the invention, synthesis of the amplification template and the detection reaction may be performed as a single step reaction (e.g., same reaction mixture and incubation step) or sequentially (e.g. separate reaction mixtures and incubation steps). In one embodiment, the second polymerase can be any polymerase which is capable of amplifying a non-modified polynucleotide template but which is not capable of amplifying a modified polynucleotide template (e.g., Pfu polymerase).

In one embodiment, the polynucleotide template is modified. The modified polynucleotide template includes one or more modifications which interfere/prevent the second polymerase from copying a nucleic acid. Suitable modifications include deoxyuracil and/or 2'-O-methyl modifications. In a preferred embodiment, the first polymerase is klenow polymerase. The first polymerase and the antibody can associate with each other as a fusion protein or they may be linked via a chemical linker. Suitable chemical linkers include biotin-streptavidin interactions. In still another embodiment, the first polymerase is coupled to the antibody via an antibody binding molecule (e.g., protein A or protein G).

The second polymerase can be any nucleic acid polymerase as long as it does not amplify/copy the modified polynucleotide template under the first primer extension reaction conditions. In one embodiment, a suitable second polymerase is Pfu DNA polymerase.

In another embodiment, the second polymerase is a chemically-treated hot start version of Taq DNA polymerase (e.g., SURESTART Taq DNA polymerase; Stratagene, La Jolla, Calif.). In this embodiment, it is preferable to remove the modified polynucleotide template prior to amplification with the second polymerase. Agents and methods suitable for the removal of the modified polynucleotide template are known in the art and include treating the sample after the first primer extension reaction but before amplification with the second polymerase with uracil deglycosylase (UDG,UNG).

The polynucleotide template is preferably free in solution, however in some embodiments it is contemplated that it is coupled to an additional antibody. Detection of the amplified template can be performed by numerous methods known in the art, including a real-time PCR detection assays (e.g. in a MX3005P real-time PCR device from Stratagene). Suitable detection assays include cleavage reactions. For example, the detection reaction may further include a labeled probe that anneals downstream of the second primer. In this embodiment, the second primer is extended so as to cleave a labeled downstream probe in a nucleic acid cleavage reaction (e.g., TAQMAN detection assay). Alternatively, the detection step may employ the direct detection of the extension product from the second primer. In this embodiment, the amplification product of the extended second primer may be detected by gel electrophoresis and visualized. The presence of the amplification product is indicative of the presence of the analyte in the sample.

In yet another aspect, the invention is directed to a composition. In this embodiment the composition includes a first analyte specific probe, second analyte specific probe, polynucleotide template, first primer complementary to the polynucleotide template, a second polymerase and a second primer complementary to an amplified template. The first ASP includes a binding moiety and a first portion of a first polymerase and the second ASP includes a binding moiety and a second portion of a first polymerase. The first and second portions of the first polymerase form a functional polymerase complex when they interact with one another.

In yet another aspect, the invention is directed to another composition. In this embodiment the composition includes a first analyte specific probe, second analyte specific probe and a second polymerase. The first ASP includes a binding moiety and a first portion of a first polymerase and the second ASP includes a binding moiety and a second portion of a first polymerase. The first and second portions of the first polymerase form a functional polymerase complex when they associate with one another.

In the compositions of the inventions, the polynucleotide template may be modified. In one embodiment, the modified polynucleotide template includes one or more deoxyuracils and 2'O-methoxy modifications. In a preferred embodiment, the first polymerase is a klenow polymerase. In yet a further embodiment, the second polymerase is a polymerase that is incapable of amplifying a modified polynucleotide template (e.g., Pfu DNA polymerase).

In yet another aspect, the invention is directed to a composition comprising a klenow fragment, wherein said klenow fragment has synthetic activity and essentially consist of an amino acid sequence which is 95% or more identical to amino acids 201-605 of SEQ ID NO:1.

In other aspects, the invention is directed to kits containing the compositions of the invention and instructions for use.

FIG. 1 illustrates one embodiment of the invention utilizing a modified polynucleotide template, a first analyte specific probe having a first binding moiety and a first portion of a first polymerase, a second analyte specific probe having a second binding moiety and a second portion of the first polymerase (e.g., klenow), and a second polymerase that is incapable of amplifying a modified polynucleotide template (e.g., Pfu DNA polymerase).

In this embodiment, a test sample containing the analyte is first reacted with the first and second analyte specific probes in a binding reaction. In some embodiment, a capture antibody bound to a solid support is also present. The first and second binding moieties are coupled to the first and second polymerase portions respectively. The binding moieties may be coupled to the polymerase portions in many different ways, including, but not limited to direct linking as an antibody/polymerase fusion protein, linked via streptavidin-biotin interactions or Protein A or Protein G. When the first and second portions of the first polymerase are separated they substantially lack synthetic activity. However, when the first and second portions of the first polymerase are brought in close proximity to each other they interact so as to form a functional first polymerase complex having synthetic activity which copies a polynucleotide template.

After binding of the ASPs and interaction of the first and second portions of the first polymerase an extension reaction proceeds. In addition to the reagents listed above, the extension reaction further includes a modified polynucleotide template and one or more additional primers that is complementary to a portion of the modified polynucleotide template. Preferably, the reaction mixture is incubated for 30 minutes at room temperature so as to permit primer annealing and extension of the primers by the first polymerase complex, so as to form an amplified template. The amplified product is then utilized in a detection reaction.

The detection reaction may be performed in the same or a different reaction vessel as the binding/extension reaction. For example, an aliquot of the reaction mixture having the amplified template may be transferred to a corresponding well of a 96-well PCR plate. In this step, the amplified template is reacted with a detection reagent (e.g., TAQMAN probe, SYBR Green dye, MOLECULAR BEACON probe), a second nucleic acid polymerase that is incapable of replicating a modified polynucleotide template and one or more additional primers. The detection reaction mixture is subjected to reaction conditions which allow annealing of the primers, amplification of the amplified template and detection of the amplified template. For example, in one embodiment the detection reaction is run in a real-time PCR device that is programmed with the appropriate times and temperatures necessary for amplification and detection. For example in a detection reaction utilizing SYBR green, a MX3005P real-time PCR device may be utilized with the program corresponding to a SYBR Green detection assay with dissociation curve and a 2-step cycling parameter of 95 C for 10 minutes, followed by 40 cycles of 95 C for 15 seconds, and 63 C for 45 seconds. Other means of real-time PCR detection are well known in the art (e.g., TAQMAN detection assay, and MOLECULAR BEACON detection assays) and can be adapted for use in the present embodiment. The detected signal can then be used to determine the concentration of the analyte in the sample.

I. Practicing the Method of the Invention

A. Test Sample and Analyte Binding

In practicing the methods of the present invention, a test sample suspected of containing the selected analyte under investigation is applied to a reaction vessel. The identity of the reaction vessel is not critical, but it should be constructed of a material to which the reagents used in the methods of the present invention do not adhere.

The quantity of test sample used is not critical, but should be an amount that can be easily handled and that has a concentration of analyte that is detectable within the limits of the methods of the present invention. For example, the quantity of the test sample may be between 2 uL and 2 mL. Preferably, the quantity of the test sample is between 2 uL and 1 mL. Most preferably, the quantity of the test sample may be between 2 uL and 200 uL.

While the concentration of the analyte in the test sample is not critical, it should be within the detection limits of the methods of the present invention. The skilled artisan will understand that the concentration may vary depending on the volume of the test sample, and thus it is difficult to provide a concentration range over which an analyte may be detected. Preferably a test sample used in the methods contains between about $1\times10^{-6}$ g and about $1\times10^{-18}$ g of the analyte, more preferably between about $1\times10^{-6}$ g and about $1\times10^{-15}$ g of the analyte, most preferably between about $1\times10^{-6}$ g and about $1\times10^{-12}$ g of the analyte.

The methods and kits taught herein can thus be used to detect analyte present in a sample at a concentration of, for example, about 10 pg/mL or less, about 1 ng/mL or less, about 0.7 ng/mL or less, about 0.5 ng/mL or less, about 0.1 ng/mL or less, about 0.01 ng/mL or less, about 1 pg/mL or less, about 0.1 pg/mL or less, about 0.01 pg/mL or less, about 1 fg/mL or less.

In some embodiments, a solid support and capture antibody are used. In this embodiment, the capture molecule is incubated with the solid support for a period of time sufficient to allow the capture molecule to bind the solid support. Alternatively an analyte is incubated with the solid support for a period of time sufficient to allow the analyte to directly bind the solid support. Preferably, the incubation proceeds from between about 10 minutes and about 60 minutes, but may require overnight.

The temperature at which each of the incubation steps of the methods is performed is not critical. Preferably, the temperature at which the incubations occur is between about 18° C. and about 37° C. More preferably, the incubation temperature is between about 18° C. and about 30° C. Most preferably, the incubation temperature is at ambient temperature (20° C.). After addition of the analyte and capture antibody a wash is generally performed followed by a detector molecule binding reaction.

B. ASP Binding and Extension Reaction

A first analyte specific probe and a second analyte specific probe are added in a suitable buffer. The first analyte specific probe has a first binding moiety and a first portion of a first polymerase while the second analyte specific probe has a second binding moiety and a second portion of the first polymerase. The first and second portions of the nucleic acid polymerase may be coupled to the first and second binding moieties respectively at the time they are added to the reaction mixture or they may be coupled during incubation with the analyte (e.g., biotin labeled antibody and added streptavidin-first and second portions of klenow).

The reaction mixture is allowed to incubate for a period of time sufficient to allow the binding moiety to bind the analyte. Preferably, the incubation proceeds from between about 5 minutes to about 60 minutes, but may require overnight.

The temperature at which each of the incubation steps of the methods are performed is not critical. Preferably, the temperature at which the incubations occur is between about 18° C. and about 37° C. More preferably, the incubation temperature is between about 18° C. and about 30° C. Most preferably, the incubation temperature is at ambient temperature (20° C.).

In one embodiment the analyte-ASP incubation reaction and extension reaction are performed simultaneously under the same reaction conditions. In another embodiment, the analyte-ASP incubation reaction and extension reaction are performed sequentially.

The extension reaction mixture includes a polynucleotide template, as described herein, and one or more primers that are complementary to a portion of the polynucleotide template. In one embodiment, the polynucleotide template is modified so as to have one or more non-conventional nucleotides.

The reaction mixture is generally incubated for 30 minutes to overnight at room temperature. During the incubation step the primer anneals to the polynucleotide template and is extended by the first nucleic acid polymerase complex so as to form an amplified template. The amplified product is then utilized in a detection reaction.

The skilled artisan will understand that the binding/primer extension conditions may vary depending on the nature and identity of the polynucleotide molecule, the primer or primers and the polymerase. The skilled artisan will understand that many other DNA polymerases, having the criteria as discussed herein (e.g., ability to amplify a modified polynucleotide template) are available that may be used in the methods of the present invention. Exemplary conditions are described in the Examples.

C. Detection Assay

After the binding/amplification reaction a detection reaction is performed. This reaction may occur in the same reaction vessel that the extension reaction occurred or in a separate reaction vessel. Preferably, the detection reaction employs polymerase chain reaction (PCR) utilizing an oligonucleotide primer or primers that are specific for the amplification template (and/or compliment thereof). PCR may be conducted directly on the assay system in a microwell plate, or in some other suitable container (such as when microbeads are used as the support).

PCR amplification buffer, an oligonucleotide primer or primers specific to the amplification product (and/or compliment thereof) and the appropriate DNA polymerase (e.g., Pfu DNA polymerase) are added. The skilled artisan will understand that the amplification buffer and DNA polymerase used in the PCR may vary depending on the nature and identity of the polynucleotide molecule portion of the amplification molecule, the nature and identity of the primer or primers and the DNA polymerase. In one embodiment, the second polymerase added to the reaction (e.g., Pfu DNA polymerase) is unable to amplify a modified polynucleotide template. An exemplary PCR amplification buffer/primer/DNA polymerase composition is 15 mM Tris-HCl pH 8.4, 50 mM KCl, 2.5 mM MgCl2, 3% DMSO, 0.01% Tween-20, 800 nM dNTPs (ACGT), Pfu(exo−) 50 U/ml (Stratagene Cat #600163-81) and 100 nM of primer in a 25 ul reaction mixture. The skilled artisan will understand that many other DNA polymerases, having the criteria discussed herein, are available for use in the methods of the present invention.

The PCR amplification may be carried out in any of the commercially available systems for performing PCR. The time and temperature of the PCR will depend on the nature and identity of the polynucleotide molecule portion of the amplification molecule and the nature and identity of the primer or primers. Exemplary conditions include 40 cycles at 95° C. (15 s) and 63° C. (45 s).

In addition to PCR amplification, the methods of the invention may be practiced using Strand Displacement Amplification (SDA), Rolling Circle Amplification (RCA), Transcription Mediated Amplification (TMA) or Ligase Chain Reaction (LCR). Amplification of signal may be generated in a homogeneous, closed tube environment, using Real-Time amplification. Instrumentation suitable for Real-Time amplification includes the ABI PRISM TaqMan system, Roche LightCycler, Idaho Technologies RapidCycler, Bio-Rad iCycler and Cepheid SmartCycler.

The amplified template may be detected during a PCR reaction by various methods known in the art. The detection of the amplified product may be detected by several means including, but not limited to, (a) direct detection of a released cleavage product on a gel; (b) indirect or direct detection of a signal generated during a nucleic acid cleavage reaction (TAQMAN reaction); (c) fluorescent change upon a probe binding a target (MOLECULAR BEACONS); or SYBR Green detection assay (e.g., see Examples). Cleavage reactions utilizing an endonuclease activity include the INVADER detection assay (Third Wave Technologies; Madison, Wis.) which is described in U.S. Pat. No. 6,348,314 and is herein incorporated by reference in its entirety. Cleavage reaction assays encompassed by the present methods also include MOLECULAR BEACON detection assays (supplied by a variety of commercial sources) and TAQMAN detection assays (supplied by a variety of commercial sources including Roche) which are described in U.S. Pat. Nos. 5,723,591; 5,925,517 and 5,804,375, each of which is herein incorporated by reference in its entirety. Cleavage reactions useful in the present invention are also described in U.S. Pat. No. 6,548,250 which is herein incorporated by reference. Such cleavage reactions may be practiced by the nuclease in the methods of the invention.

In embodiments which utilize a solid support and a capture antibody, between the additions of reagents in the methods of the present invention, the assay system is preferably subjected to washing to reduce the incidence of non-specific binding. Stringent wash conditions which do not cause dissociation of the ASP-analyte and first polymerase complex can be employed. For example, heating, pH changes, or (and) the addition of formamide, detergents and salts can be used to increase the efficiency of the wash step. Too stringent conditions can lead to dissociation of the ASP-analyte and first polymerase complexes or destruction of the reporter. Tolerance to stringent wash conditions will vary with the nature of the analyte, binding member, reactive moeity and specific reporter used. The stringent conditions must, therefore, be experimentally optimized for each assay. However, in washing to reduce non-specific binding, if some of the ASP-analyte and polymerase complexes are lost, this can be compensated for by additional target replication realized by increasing the number of temperature recycle steps or increasing the time of the primer extension step While the number of wash cycles and soak times is empirically determined, in general either water or a low or high molarity salt solution with a detergent such as Tween 20, Triton X-100, or NP-40 may be used as the washing solution. 1-8 washes, each lasting 5 seconds to 10 minutes may be performed, after incubation of each of the reagents used in the methods. The detergent concentration is typically 0 to 0.1% with a salt concentration of 0 to 100 nM (e.g., NaCl). Preferably, washing takes place between each incubation step, e.g., after addition of the capture molecule to the solid support, after addition of the test sample and after addition of the detector molecule. Exemplary washing conditions are described in the Examples.

II. Analytes

The invention may be used to detect a wide variety of analytes. The binding sites for each ASPs can be the same or different. An analyte can be a single molecule, molecular complex, an organism or virus containing multiple reagent binding sites. Since the length of the oligonucleotides of the ASPs can be constructed to span varying molecular distances, binding sites need not be on the same molecule. However, they may be on separate, but closely positioned, molecules. For example, the multiple binding epitopes of an organism, such as a virus, bacteria or cell can be targeted by the methods of the invention.

III. Binding Molecules

The methods of the present invention may be adapted for the detection of any analyte by simply altering the binding moiety used in the method such that the binding moiety utilized specifically recognize and binds the analyte for which the method is being used.

The binding moieties are designed so as to bind within close proximity to one another so as to allow the first and second portions of the first nucleic acid polymerase to interact so as to form an amplification template.

The first and second binding moieties may recognized and bind the same portion or epitope of the analyte under investigation (e.g., multivalent analyte). Alternatively, the first and second binding moieties recognize and bind different portions or epitopes of the analyte. In some embodiments, the first and second binding moieties may not bind to the same analyte but two different analytes that interact to form a complex. For example, a first binding moiety may be specific for and bind to a receptor protein and the second binding moiety may be specific for and bind to a ligand of the receptor such that the first binding moiety, receptor protein, ligand and second binding moiety form a complex.

The specific molecules used as the binding moieties used in the methods of the present invention are not particularly limited. Molecules useful as the binding moieties include monoclonal, polyclonal, or phage derived antibodies, antibody fragments, peptides, ligands, haptens, nucleic acids, nucleic acid aptamers, protein A, protein G, folate, folate binding proteins, plasminogen, maleimide and sulfhydryl reactive groups, and those that may be produced for use with the methods of the present invention.

Preferably, the binding moieties are monoclonal, polyclonal, or phage derived antibodies, or antibody fragments. More preferably, the capture and detector molecules are monoclonal antibodies.

Antibodies, whether they are polyclonal, a monoclonal or an immunoreactive fragment thereof, can be produced by customary methods familiar to those skilled in the art. Conventional monoclonal and polyclonal antibodies are of use and represent a preferred type binding molecule. Established methods of antibody preparation therefore can be employed for preparation of the immune type binding molecules. Suitable methods of antibody preparation and purification for the immune type binding moieties are described in Harlow, Ed and Lane, D in Antibodies a Laboratory Manual, Cold Spring Harbor Laboratory Press, Cold Spring Harbor, N.Y. (1988). Furthermore, the assays described herein can be used with currently available commercially available antibodies.

"Polyclonal antibodies" are heterogeneous populations of antibody molecules derived from the sera of animals immunized with an antigen, or an antigenic functional derivative thereof. For the production of polyclonal antibodies, host animals such as rabbits, mice and goats, may be immunized by injection with an antigen or hapten-carrier conjugate optionally supplemented with adjuvants.

Any method known in the art for generating monoclonal antibodies are contemplated, for example by in vitro generation with phage display technology and in vivo generation by immunizing animals, such as mice, can be used in the present invention. These methods include the immunological methods described by Kohler and Milstein (*Nature* 256, 495-497 (1975)) and Campbell ("Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam (1995)); as well as by the recombinant DNA method described by Huse et al. (*Science* 246, 1275-1281 (1989)). Standard recombinant DNA techniques are described in Sambrook et al. ("Molecular Cloning," Second Edition, Cold Spring Harbor Laboratory Press (1987)) and Ausubel ("Current Protocols in Molecular Biology," Green Publishing Associates/Wiley-Interscience, New York (1990)). Each of these methods is incorporated herein by reference.

The capture molecule and the detector molecule are not limited to intact antibodies, but encompass other binding molecules such as antibody fragments and recombinant fusion proteins comprising an antibody fragment.

As used herein, "antibody" includes any portion of an antibody that retains the ability to bind to the epitope recognized by the full length antibody, generally termed "epitope-binding fragments." Examples of antibody fragments preferably include, but are not limited to, Fab, Fab', and F(ab')$_2$, Fd, single-chain Fvs (scFv), single-chain antibodies, disulfide-linked Fvs (sdFv) and fragments comprising either a $V_L$ or $V_H$ domain. Epitope-binding fragments, including single-chain antibodies, may comprise the variable region(s) alone or in combination with the entirety or a portion of the following: hinge region, $C_H1$, $C_H2$, and $C_H3$ domains.

Methods of producing chimerized, humanized, and single-chain antibodies as well as fragments thereof are disclosed in PCT Application WO 93/21319, European Patent Application No. 239,400; PCT Application WO 89/09622; European Patent Application 338,745; and European Patent Application EP 332,424. Each of these methods is incorporated herein by reference.

In addition, techniques developed for the production of "chimeric antibodies" (Morrison, et al., Proc. Natl. Acad. Sci., 81:6851-6855 (1984); Takeda, et al., Nature, 314:452-54(1985)) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, Science 242:423-26 (1988); Huston, et al., Proc. Natl. Acad. Sci. USA, 85:5879-83 (1988); and Ward, et al., Nature, 334:544-46 (1989)) can be adapted to produce gene-single chain antibodies. Single chain antibodies are typically formed by linking the heavy and light chain fragments of the Fv region via an amino acid bridge, resulting in a single chain polypeptide.

Non-immune binding-molecules are also contemplated for use as binding moieties. These molecules include systems, wherein, two components share a natural affinity for each other, but are not antigen/antibody-like pairs. Exemplary non-immune binding-moieties include biotin/avidin or biotin/streptavidin, folic acid-folate binding protein, vitamin B12/intrinsic factor, complementary probe nucleic acids, Proteins A, G, immunoglobulins, hetero- and homo-dimeric polypeptide complexes, etc. Also included are non-immune binding-pairs that form a covalent bond with each other.

One could also use non-antibody protein receptors or non-protein receptors such as polynucleic acid aptimers. Polynucleic acid aptimers are typically RNA oligonucleotides which may act to selectively bind proteins, much in the same manner as a receptor or antibody (Conrad et al., Methods Enzymol. (1996), 267(Combinatorial Chemistry), 336-367). Theses aptimers will be suitable in the present invention as binding molecules.

By the terms "specifically binding" and "specific binding" as used herein is meant that an antibody or other binding molecule, especially a receptor of the invention, binds to a target such as an antigen, ligand or analyte, with greater affinity than it binds to other molecules under the specified conditions of the present invention. Antibodies or antibody fragments, as known in the art, are polypeptide molecules that contain regions that can bind other molecules, such as antigens. In various embodiments of the invention, "specifically binding" may mean that an antibody or other biological molecule, binds to a target molecule with at least about an affinity of $10^{-6}$-$10^{-10}$/M, more preferably they will have an affinity of at least $10^{-8}$/M, most preferably they will have an affinity at least $10^{-9}$/M.

IV. Polymerases

DNA polymerases are well known to those skilled in the art. These include both DNA-dependent polymerases and RNA-dependent polymerases such as reverse transcriptase. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases.

Similarly, RNA polymerases typically include eukaryotic RNA polymerases I, II, and III, and bacterial RNA polymerases as well as phage and viral polymerases. RNA polymerases can be DNA-dependent and RNA-dependent.

In specific embodiments, Taq polymerase is split into a first and second portion which are linked to a binding moiety (antibody). Other family A polymerases that act similarly to Taq, e.g., *Thermus brockianus* polymerase, which is about 90% similar to Taq polymerase, as well as *Thermus flavus* polymerase, and *Thermus thermophilus* polymerase, which has reverse transcriptase activity, may also be used. Additionally, less extremely thermophilic polymerases, such as the family A polymerase from *Bacillus stearothermophilus* are likely to prove useful, as are mesophilic polymerases such as *E. coli* Pol I.

Family B polymerases such as *Pyrococcus polymerases*, e.g., Pfu polymerase, are useful as the second polymerase of the invention.

The activity of a polymerase can be measured using assays well known to those of skill in the art. For example, a processive enzymatic activity, such as a polymerase activity, can be measured by determining the amount of nucleic acid synthesized in a reaction, such as a polymerase chain reaction. In determining the relative efficiency of the enzyme, the amount of product obtained with a polymerase containing a sequence-non-specific double-stranded DNA binding domain can then be compared to the amount of product obtained with the normal polymerase enzyme.

A polymerase domain suitable for use in the invention can be the enzyme itself or the catalytic domain, e.g., klenow polymerase or a fragment of klenow with polymerase activity. The catalytic domain may include additional amino acids and/or may be a variant that contains amino acid substitutions, deletions or additions, but still retains enzymatic activity.

In one embodiment, the polymerase is divided into two portions that do not have substantial synthetic activity when separated but do have substantial synthetic activity when they interact to form a complex. The first polymerase may be split into two portions which are each coupled to a separate antibody. In one embodiment, the first polymerase is klenow. In a preferred embodiment, the first portion of the first polymerase comprises amino acid residues 1-225 corresponding to SEQ ID NO:1 and the second portion of the first polymerase comprises amino acid residues 225-605 corresponding to SEQ ID NO:1.

The term "klenow" refers to polypeptide polymorphic variants, alleles, mutants, and interspecies homologs that have an amino acid sequence that has greater than about 70%, 75%, 80%, 85%, 90%, preferably 91%, 92%, 93%, 94%, 95%, 96%, 97%, 98% or 99% or greater amino acid sequence identity, preferably over a region of at least about 25, 35, 50, or more amino acids, to the klenow sequence of SEQ ID NO:1 and which display synthetic activity.

Suitable cleavage sites for constructing first and second portions of a first polymerase other than klenow can be identified based on their sequence homology to klenow. The test sequence can be compared and aligned with the klenow sequence for maximum correspondence over a comparison window, or designated region as measured using one of the following sequence comparison algorithms or manual alignment and visual inspection. Percent amino acid identity can be determined by the default parameters of BLAST. For example, other Family A polymerases may be cleaved into a first portion which corresponds to amino acid residues 1-225 of SEQ ID NO:1 and into a second portion which corresponds to amino acid residues 225-605 of SEQ ID NO:1. In yet another embodiment, the test polymerase is cleaved into two portions at an amino acid corresponding to any one of amino acids 199-310 of SEQ ID NO:1.

As used herein, the term "corresponding to" refers to one or more amino acids in a test polypeptide sequence (Family A polymerase) that aligns with a given amino acid(s) in a reference polypeptide sequence (e.g., klenow, SEQ ID NO:1) when the first polypeptide and reference polypeptide sequences are aligned. Alignment is performed by one of skill in the art using software designed for this purpose, for example, BLASTP version 2.2.2 with the default parameters for that version.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The comparison window includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An example of an algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l Acad. Sci. USA* 90:58735787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Polymerase alignments for the Family A and Family B DNA polymerases are found in FIG. 1 of Braithwaite and Ito., *Nucleic acids Research.* 21(4); 787-802 (1993), which is herein incorporated by reference.

Polymerases capable of replicating a modified polynucleotide template are preferred in practicing some embodiments of the methods of the invention. Polymerases capable of replicating a modified polynucleotide template include klenow (exo−) and (exo+) and T4. Other polymerases that may be suitable for replicating a modified polynucleotide template include Family A DNA polymerases, including Taq and T7. Such polymerases are well known in the art and can be tested in the assays described herein to determine their suitability for use in the methods described herein. For example, one may determine whether a particular test polymerase is capable or incapable of replicating a modified polynucleotide template by incubating the test polymerase with a modified polynucleotide template under conditions suitable for amplification. Such conditions are known in the art and readily accessible for commercially available polymerases. For example, a suitable reaction mixture can include (all conc. are final after mixing):

15 mM Tris-HCl pH 8.4
50 mM KCl
2.5 mM MgCl2
3% DMSO
0.01% Tween-20
800 nM dNTPs (ACGT)
0.444×SYBR Green (Molecular Probes, provided as 10,000×)
30 nM Rox reference dye (Stratagene Cat #600530)
Various concentrations of enzyme, e.g., 50 U/ml
100 nM Forward primer
100 nM Reverse primer
40 pM Oligo1 modified and its complementary sequence:
5'-TTTTTTTGCTCGACGGTGAAUGAUGTAG-GUACCAGC AGUAACUCGAGCACGUCUU 2'OMe (CG)A 2'OMe(CC) AAAUCUGGAUAUUGCAGC-CTCGT-3'
83 mer phosphodiester DNA/2'OMe; U indicates 2'deoxyuridine A QPCR can then be performed in an MX3005P using the program for SYBR green with dissociation curve and the default cycling parameters of [95 C for 10 min] (1 cycle), [95 C for 30 sec, 55 C for 60 sec, 72 C for 30 sec] (40 cycles).

Detection of an amplification product indicates the polymerase is capable of replicating a modified polynucleotide template while no amplification indicates the polymerase is incapable of replicating a modified polynucleotide template.

Polymerases not capable of replicating a modified polynucleotide template are preferred in practicing some embodiments of the methods of the invention. Polymerases incapable of replicating a modified polynucleotide template include Pfu DNA polymerase. It is contemplated that other Family B DNA polymerases are also useful in practicing the invention in embodiments in which a polymerase not capable of replicating a modified polynucleotide template are required. Such polymerases include human α, δ and ε DNA polymerases, RB69 and Phi29 bacteriophage DNA polymerase The polymerases may be coupled to Streptavidin or Protein G or A. For example, a first and second portion of klenow or T4 may be fused to Streptavidin or Protein G. Methods of making polymerase fusion proteins are known in the art and described herein.

Additional polymerases that fall within one of the above mentioned categories are known in the art. In addition, polymerases can be tested for any of the above activities by assays known in the art and described herein. Buffer and extension temperatures are selected to allow for optimal activity by the particular polymerase useful according to the invention. Buffers and extension temperatures useful for polymerases according to the invention are know in the art and can also be determined from the Vendor's specifications.

V. Oligonucleotides/Polynucleotides

The terms "polynucleotide", "oligonucleotide" and "nucleic acid (molecule)" are used interchangeably to refer to polymeric forms of nucleotides of any length. The polynucleotides may contain deoxyribonucleotides, ribonucleotides and/or their analogs. Nucleotides may have any three-dimensional structure, and may perform any function, known or unknown. The term "polynucleotide" includes single-, double-stranded and triple helical molecules. Polynucleotides may be isolated from genes, or chemically synthesized by methods known in the art.

The invention provides for oligonucleotide primers and probes useful for detecting or measuring a nucleic acid, for amplifying a template nucleic acid sequence, and for forming a cleavage structure according to the invention.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification. In some embodiments, the primer may have a 3' flap which is cleaved by a 3' nuclease.

Oligonucleotide primers useful according to the invention are single-stranded DNA or RNA molecules that are hybridizable to a template nucleic acid sequence and prime enzymatic synthesis of a second nucleic acid strand. The primer is complementary to a portion of a target molecule. It is contemplated that oligonucleotide primers according to the invention are prepared by synthetic methods, either chemical or enzymatic. Alternatively, such a molecule or a fragment thereof is naturally-occurring, and is isolated from its natural source or purchased from a commercial supplier. Oligonucleotide primers and probes are 5 to 100 nucleotides in length, ideally from 17 to 40 nucleotides, although primers and probes of different length are of use. Primers for amplification are preferably about 17-25 nucleotides. Primers useful according to the invention are also designed to have a particular melting temperature (Tm) by the method of melting temperature estimation. Commercial programs, including Oligo, Primer Design and programs available on the internet, including Primer3 and Oligo Calculator can be used to calculate a Tm of a nucleic acid sequence useful according to the invention. Preferred, Tm's of a primer will depend on the particular embodiment of the invention that is being practiced. For example, in one embodiment the primer will dissociate from a target at a temperature of 41° C. or more. While in other embodiments it is preferable to have a Tm between about 45 and 65° C. and more preferably between about 50 and 60° C. The oligonucleotides of the invention include polynucleotide templates (modified or non-modified) and primers. The polynucleotide templates can be prepared with lengths ranging in length from at least 10 bases in length, typically at least 20 bases in length, for example, at least 30, 40, 50, 60, 70, 80, 90 or 100 bases in length. While the oligonucleotide can be large nucleic acid fragments, it is generally limited to nucleic acids of 500 bases or less.

The oligonucleotides of the invention may be free in solution or conjugated to a binding molecule. Oligonucleotides that are conjugated to a binding moiety will generally have a chemically active group (such as, primary amine group) at any point in its stretch of nucleic acids, which allows it to be conjugated.

As used herein, "modification" or "modified" refers to any change in a polynucleotide template (e.g., addition of non-conventional nucleotides) which renders the nucleic acid non-amplifiable by a specific class of polymerases (e.g., Pfu (exo−) but amplifiable by other polymerases (e.g., klenow). Such modifications include replacing nucleic acid phosphates with a thiophosphates and replacing the 2' hydroxyls with 2'-O-methyl. Other suitable modifications include one or more of the following: 2'-deoxy-2'-fluoro-β-D-arabinonucleic acid (2'F-ANA) nucleotides, locked-nucleic acids (LNAs) and ENAs: 2'-O,4'-C-ethylene-bridged nucleic acids, reversed deoxyribonucleotides, dU, hypoxanthine, 8-oxo-guanine, 8-oxo-adenine, ethenoadenine, apurinic sites, cholesterol adducts and other non-conventional nucleotides, e.g., such as those available from TriLink BioTech (San Diego, Calif.), PerkinElmer Life And Analytical Sciences, Inc. (Waltham, Mass.) and Sigma-Aldrich (St. Louis, Mo.).

A "non-conventional nucleotide" or "non-natural nucleotide" refers to a) a nucleotide structure that is not one of the four conventional deoxynucleotides dATP, dCTP, dGTP, and dTTP recognized by and incorporated by a DNA polymerase, b) a synthetic nucleotide that is not one of the four conventional deoxynucleotides in (a), c) a modified conventional nucleotide, or d) a ribonucleotide (since they are not normally recognized or incorporated by DNA polymerases) and modified forms of a ribonucleotide. These modified nucleotides can be tested via the methods described herein for their usefulness in embodiments of the invention utilizing a modified polynucleotide template.

As used herein "modified polynucleotide template" as used herein refers to a polynucleotide template which is modified, as defined herein, so that it can not be copied by a particular class of polymerase (e.g., Pfu (exo−)) but is capable of being copied by another class of polymerases (e.g., klenow) under reaction conditions routinely used for the particular polymerase of interest. For example, a modified polynucleotide template can not be replicated by a Pfu DNA polymerase under reaction conditions suitable for Pfu DNA polymerase (e.g., 1× Pfu buffer at 60-72° C.) but can be replicated by klenow under conditions suitable for klenow (10 mM Tris-HCl (pH 7.5), 5 mM MgCl2, 7.5 mM DTT at room temperature).

The modified polynucleotide must not result in more than 10%, 5%, 1%, 0.5%, 0.1% and most preferably 0% of the amount of amplification product as produced with a non-modified polynucleotide template and the same polymerase (e.g., Pfu). One of ordinary skill in the art can determine whether a polymerase is capable of copying a modified polynucleotide template by nucleic acid polymerase assays known in the art. For example, in order to determine whether a particular polymerase is capable of amplifying a modified polynucleotide template the polymerase can be incubated with a modified polynucleotide template described herein in a primer extension reaction and the resulting product detected. The presence of amplification product indicates the polymerase is capable of copying a modified polynucleotide template while the absence of the amplification product indicates the polymerase is incapable of copying the modified polynucleotide template.

As noted above, the polynucleotide template is replicated to produce an amplification template. The design of the polynucleotide template is important because replication requires suitable complementary primer(s); and also because the polynucleotide template can provide for different means of detection and for flexibility in reaction conditions. For example, in some embodiments the polynucleotide template is modified.

The polynucleotide template may be double-stranded (ds), comprising a hybrid duplex of two complementary nucleic acid strands, or may alternatively, be single-stranded (ss). Either or both strands can carry modified bases.

In one embodiment, logarithmic replication can be achieved using a single-stranded polynucleotide template and a single primer. This is achieved by designing the polynucleotide template sequence to contain a primer binding sequence at one end of the ss target and a complement sequence of the primer binding site at the opposite end of the target strand. Annealing and extension of the primer will result in the formation of a complementary target strand containing the identical primer binding sites. In this way both the (+) and (−) strands of the resulting ds target contain an identical primer site at opposite ends of the target duplex, and the same primer used in combination with the polymerase and target nucleic acid promotes replication of both + and − target strands.

In other preferred embodiments, the base composition and sequence of the polynucleotide template sequence can be varied to accommodate different assay requirements. For example, the polynucleotide template may contain one or more modified nucleotides as described herein, so as to prevent replication by certain classes of polymerases (e.g., Pfu polymerase).

It is contemplated, for example, that a polynucleotide template sequence may be designed to contain a coupling linkage for the attachment of a detection molecule at the 5' end and a primer binding site at the 3' end with a variable region inserted between. Alternatively, the coupling linkage can be at the 3' end of the polynucleotide. The variable region could be of any length or composition, limited only by the requirements of the polynucleotide template amplification method. For example, an oligonucleotide can be conjugated to an antibody through a chemical coupling linkage at the 5' end. The polynucleotide template may contain a 5' binding region complementary to one of the replication primers, and a 3' site for binding the other replicated primer. The polynucleotide template may have a variable region of nucleic acid bases, which could be variable in length or in sequence, thereby providing alternative means of detection of the replicated targets based on size or other factors, including different sequences that are detected during the detection amplification reaction with specific primers and/or probes.

In another embodiment, a series of different polynucleotide templates are utilized for different analytes for use in a multi-plex assay. For example, a series of polynucleotide templates differing in either the primer binding site and/or the inner polynucleotide template region could be prepared, and coupled to different binding molecules which are capable of binding to different analytes. The replication products of each of these receptor conjugates (e.g., amplification product) could then be readily distinguished on the basis of size, or sequence in the detection reaction. For example amplification template specific primers and/or probes with different reporter molecules that can be used to distinguish a variety of different amplification products that may be present in a multi-plex reaction. Thus, multiple analytes could be detected in a real-time PCR reaction.

VI. Coupling Polymerases and Polynucleotides to Binding Molecules and Expression Thereof In practicing the present invention, at least two different types of linkings are contemplated. The first linking type comprises an enzyme (e.g., polymerase) coupled to an antibody or other binding molecule. These may be prepared using methods well known to those skilled in the art. D. G. Williams, J. Immun. Methods, 79, 261 (1984). Alternatively, enzyme-binding conjugates can be generated using recombinant DNA and genetic engineering techniques. I. Pastan and D. Fitzgerald, Science, 254, 1173 (1991). Enzymes suitable for use in the antibody conjugate include, but are not limited to polymerases (e.g., polymerases capable of replicating a modified polynucleotide template). The choice of polymerase conjugate depends upon which embodiment of the present invention is practiced.

Extensive guidance can be found in the literature for covalently linking proteins to binding compounds, such as antibodies, e.g. Hermanson, Bioconjugate Techniques, (Academic Press, New York, 1996), and the like. In one aspect of the invention, one or more proteins are attached directly or indirectly to common reactive groups on a binding moiety. Common reactive groups include amine, thiol, carboxylate, hydroxyl, aldehyde, ketone, and the like, and may be coupled to proteins by commercially available cross linking agents, e.g. Hermanson (cited above); Haugland, Handbook of Fluorescent Probes and Research Products, Ninth Edition (Molecular Probes, Eugene, Oreg., 2002). In one embodiment, an NHS-ester of a molecular tag is reacted with a free amine on the binding molecule.

The second type consists of a polynucleotide template sequence coupled to an antibody or other binding molecule which recognizes an analyte. These can be prepared using variations of methods known to those skilled in the art for linking proteins to amino-oligonucleotides. For example, this may be accomplished using enzymatic tailing methods in which an amino-modified dNTP is added onto the 3' end of the nucleic acid. A. Kumar, Anal. Biochem., 169, 376 (1988). Alternatively, amino-modified bases can be synthetically introduced into the nucleic acid base sequence. P. Li, et al., Nucleic Acids Res., 15, 5275 (1987). Antibodies can then be attached to amino-modified nucleic acids by substituting an antibody for an enzyme in the method of Urdea. M. S, Urdea, Nucleic Acids Res., 16, 4937 (1988).

In some embodiments, the nucleic acid/antibody conjugates involves the coupling of heterobifunctional cross-linkers to the DNA oligonucleotide targets which in turn are coupled to antibodies using chemistry described by Tseng et. al. in U.S. Pat. No. 5,324,650.

To facilitate the chemical attachment of the oligonucleotides to the antibodies, the oligonucleotides may be amino-modified by introducing a primary amine group at their 5' end during synthesis using cyanoethyl-phosphoramidite chemistry. The amino-modified oligonucleotides may be further modified with a hetero-bifunctional reagent that introduces sulfhydryl groups. The reagent, N-succinimidyl S-acetylthioacetate (SATA) is a heterobifunctional cross-linker agent that uses the primary amine reactive group, N-hydroxyl-succinimide (NHS) to couple to the amino-modified oligonucleotides introducing an acetyl-protected sulfhydryl group. The antibodies are modified with another NHS cross-linking agent, succinimidyl 4-(N-maleimidomethyl) cyclohexane-1-carboxylate (SMCC). The SMCC reacts with primary amine groups within the peptides (e.g., the .epsilon.-groups on lysine) of the antibody, introducing a maleimide group (a free sulfhydryl reactive group) to the antibody. The maleimide-modified antibodies are mixed with the SATA modified antibodies. The acetyl-protected sulfhydryl groups on the SATA-modified oligonucleotides are activated with the addition of hydroxylamine to produce reactive, free sulfhydryl groups (U.S. Ser. No. 07/946,247). The free sulfhydryl-containing oligonucleotides react immediately with maleimide-modified antibodies forming DNA to antibody conjugates.

The oligonucleotides of the invention can be attached to the binding molecules at the oligonucleotide's 5' nucleotide, 3' nucleotide or at an internal nucleotide. Alternatively, the oligonucleotides are attached indirectly to the binding molecule via streptavidin, protein A or protein G. For example, the oligonucleotides can be conjugated to antibodies via biotin-streptavidin.

The ASPs of the invention include a binding moiety and a reactive moiety. In a preferred embodiment, the binding moiety is an antibody and the reactive moiety is a first or second portion of a polymerase. In yet a further embodiment, the antibody and first or second portion of the polymerase is a fusion polypeptide.

Polymerase/antibody fusion proteins comprises a polypeptide chain comprising a first polypeptide sequence of an antibody of interest or an active fragment thereof and a second polypeptide sequence a first or second portion of a polymerase. The antibody-fusion polypeptides described herein can be made using methods known in the art. For example, the fusion proteins of the invention may be constructed as described in U.S. Pat. No. 6,194,177.

In general, a nucleic acid molecule encoding the antibody of interest is cloned by PCR and ligated, in frame, with a nucleic acid molecule encoding the first or second portion of the polymerase. The nucleic acid molecule encoding the fusion/hybrid protein is subsequently transfected into a host cell for expression. The sequence of the final construct can be confirmed by sequencing.

Nucleic acids encoding the polymerase portions to be incorporated into antibody-polymerase hybrids of the invention can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999).

Nucleic acid sequences encoding polymerases useful in practicing the invention can be obtained using any of a variety of methods. In some embodiments, the nucleic acid sequences encoding the polypeptides are cloned from cDNA and genomic DNA libraries by hybridization with probes, or isolated using amplification techniques with oligonucleotide primers. More commonly, amplification techniques are used to amplify and isolate the polymerase sequences using a DNA or RNA template (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding polymerase can also be isolated from expression libraries using antibodies as probes.

The antibodies and polymerase can be linked either directly or via a covalent linker, e.g., an amino acid linker, such as a polyglycine linker, or another type of chemical linker, e.g., a carbohydrate linker, a lipid linker, a fatty acid linker, a polyether linker, e.g., PEG, etc. (See, e.g., Hermanson, Bioconjugate techniques (1996)). The polypeptides forming the ASPs are typically linked C-terminus to N-terminus, although they can also be linked C-terminus to C-terminus. The different chains of amino acids in a fusion protein may be directly spliced together or may be indirectly spliced together via a chemical linking group or an amino acid linking group, which can be about 200 amino acids or more in length, with 1 to 100 amino acids being typical. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

In some embodiments, the amino acid sequence of the antibody or binding fragment thereof is linked to a portion of a polymerase via a peptide linker. Exemplary peptide linkers are well known in the art and generally comprise several Gly and several Ser residues, e.g., such as GlyGlyGlySerSerGlyGlyGlySerGly. In one embodiment, a peptide linker for use in an ASP protein of the invention acts as a flexible hinge.

Preferably the first or second portion of the polymerase is linked to the non-antigen binding portion of the antibody. In a more preferred embodiment, the first or second portion of the polymerase is linked to the c-terminus of the binding moiety.

In one embodiment, the invention is directed to an antibody coupled to a klenow that is 95% or more identical to the amino acid sequence of SEQ ID NO:1, In another embodiment, the invention is directed to a first portion of a first polymerase that is 95% or more identical to the amino acid sequence of SEQ ID NO:2

In another embodiment, the invention is directed to a second portion of a first polymerase that is 95% or more identical to the amino acid sequence of SEQ ID NO:3

In another embodiment, the invention is directed to a first portion of a first polymerase that is 98% or more identical to the amino acid sequence of SEQ ID NO:2.

In another embodiment, the invention is directed to a second portion of a first polymerase that is 98% or more identical to the amino acid sequence of SEQ ID NO:3

In another embodiment, the invention is directed to a first portion of a first polymerase that is 99% or more identical to the amino acid sequence of SEQ ID NO:2.

In another embodiment, the invention is directed to a second portion of a first polymerase that is 99% or more identical to the amino acid sequence of SEQ ID NO:3.

In order to express the ASPs of the invention, DNA molecules obtained by any of the methods described herein or those that are known in the art, can be inserted into appropriate expression vectors by techniques well known in the art. For example, a double stranded cDNA can be cloned into a suitable vector by homopolymeric tailing or by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention comprises vectors (e.g., recombinant plasmids and bacteriophages) that include nucleic acid molecules (e.g., genes or recombinant nucleic acid molecules comprising genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived.

For eukaryotic hosts, different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples include, but are not limited to, the TK promoter of the Herpes virus, the SV40 early promoter, the yeast ga14 gene promoter, etc. Transcriptional initiation regulatory signals may be selected which allow for repression or activation, so that expression of the genes can be modulated.

In some embodiments, one or more DNA molecules comprising a nucleotide sequence encoding one or more polypeptide chains of a hybrid protein are operably linked to one or more regulatory sequences, which are capable of integrating the desired DNA molecule into a host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use, if necessary.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

Host cells may either be prokaryotic or eukaryotic. Examples of eukaryotic host cells include, for example, mammalian cells, such as human, monkey, mouse, and Chinese hamster ovary (CHO) cells. Such cells facilitate post-translational modifications of proteins, including, for example, correct folding or glycosylation. Additionally, yeast cells can also be used to express hybrid proteins of the invention. Like most mammalian cells, yeast cells also enable post-translational modifications of proteins, including, for example, glycosylation. A number of recombinant DNA strategies exist which utilize strong promoter sequences and high copy number plasmids that can be utilized for production of proteins in yeast. Yeast transcription and translation machinery can recognize leader sequences on cloned mammalian gene products, thereby enabling the secretion of peptides bearing leader sequences (i.e., pre-peptides). A particularly preferred method of high-yield production of the hybrid proteins of the invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

After the introduction of one or more vector(s), host cells are usually grown in a selective medium, which selects for the growth of vector-containing cells. Purification of the recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

VII. Capture Molecules Attached to Solid Surface

In one embodiment, the invention is practiced in the presence of a solid support. As used herein, a "solid support" or "solid surface" refers to any structure that provides a support for the capture molecule (e.g., antibody). As used herein, the term "capture antibody" or "capture molecule" refers to a molecule including monoclonal, polyclonal, or phage derived antibodies and binding fragments thereof which bind an analyte and are coupled to a solid support. Suitable solid supports include polystyrene, derivatized polystyrene, a membrane, such as nitrocellulose, PVDF or nylon, a latex bead, a glass bead, a silica bead, paramagnetic or latex microsphere, or microtiter well. As a further example, the solid support may be a modified microtiter plate, such as a Top Yield plate, which allows for covalent attachment of a capture molecule, such as an antibody, to the plate. When the solid support is a material such as a bead, paramagnetic microsphere or latex microsphere, the solid support may be contained in an open container, such as a multi-well tissue culture dish, or in a sealed container, such as a screw-top tube, both of which are commonly used in laboratories.

The solid support may be modified to facilitate binding of the capture molecule to the surface of the support, such as by coating the surface with poly L-lysine, or siliconized with amino aldehyde silane or epoxysilane. The skilled artisan will understand that the circumstances under which the methods of the current invention are performed will govern which solid supports are most preferred and whether a container is used.

Quantities of the capture molecule to be attached to the solid support may be determined empirically by checkerboard titration with different quantities of analyte that would be expected to mimic quantities in a test sample. Generally, the quantity of the analyte in the test sample is expected to be in the attogram to milligram range. An unknown concentration of the analyte in a test sample will be added at specified volumes, and this will influence the sensitivity of the test. If large volumes of the test sample (e.g., 200-400 uL) are used, modification of the test format may be needed to allow for the larger sample volumes. Generally, however, the concentration of the capture molecule will be about 1 to about 10 micrograms per mL.

The capture molecule can be attached to a solid support by routine methods that have been described for attachment of an analyte to plastic or other solid support systems (e.g., membranes or microspheres). Examples of such methods may be found in U.S. Pat. No. 4,045,384 and U.S. Pat. No. 4,046,723, both of which are incorporated herein by reference.

Attachment of the capture molecule to surfaces such as membranes, microspheres, or microtiter wells may be performed by direct addition in PBS, or other buffers of defined pH, followed by drying in a convection oven.

The capture molecule may be attached to the solid support by an attachment means, such as via adsorption, covalent linkage, avidin-biotin linkage, streptavidin-biotin linkage, heterobifunctional cross-linker, Protein A linkage or Protein G linkage. Each of the attachment means should permit the use of stringent washing conditions with minimal loss of the capture molecule from the surface of the solid support. As an example, the adsorption may be hydrophilic adsorption. As a further example, the heterobifunctional cross-linker may be maleic anhydride, 3-aminopropyl trimethoxysilane (APS), N-5 azido, 2-nitrobenzoyaloxysuccinimide (ANB-NOS) or mercaptosilane.

The capture molecule may be attached to the solid support though a portion of the capture molecule, such as an amino acid residue, preferably a lysine or arginine residue, a thiol group or a carbohydrate residue. When the capture molecule is an antibody, the thiol group may be a thiol group of the antibody hinge region.

The solid support may be derivatized with avidin or streptavidin, and the capture molecule may be modified to contain at least one biotin moiety, to aid in the attachment of the capture molecule to the solid support. Alternatively, the solid support may be derivatized with biotin, and the capture molecule may be modified to contain at least one avidin or at least one streptavidin moiety.

EXAMPLES

Example 1

Reconstitution of Klenow Activity in the Presence of Biotinylated Antibody

Figure 2:
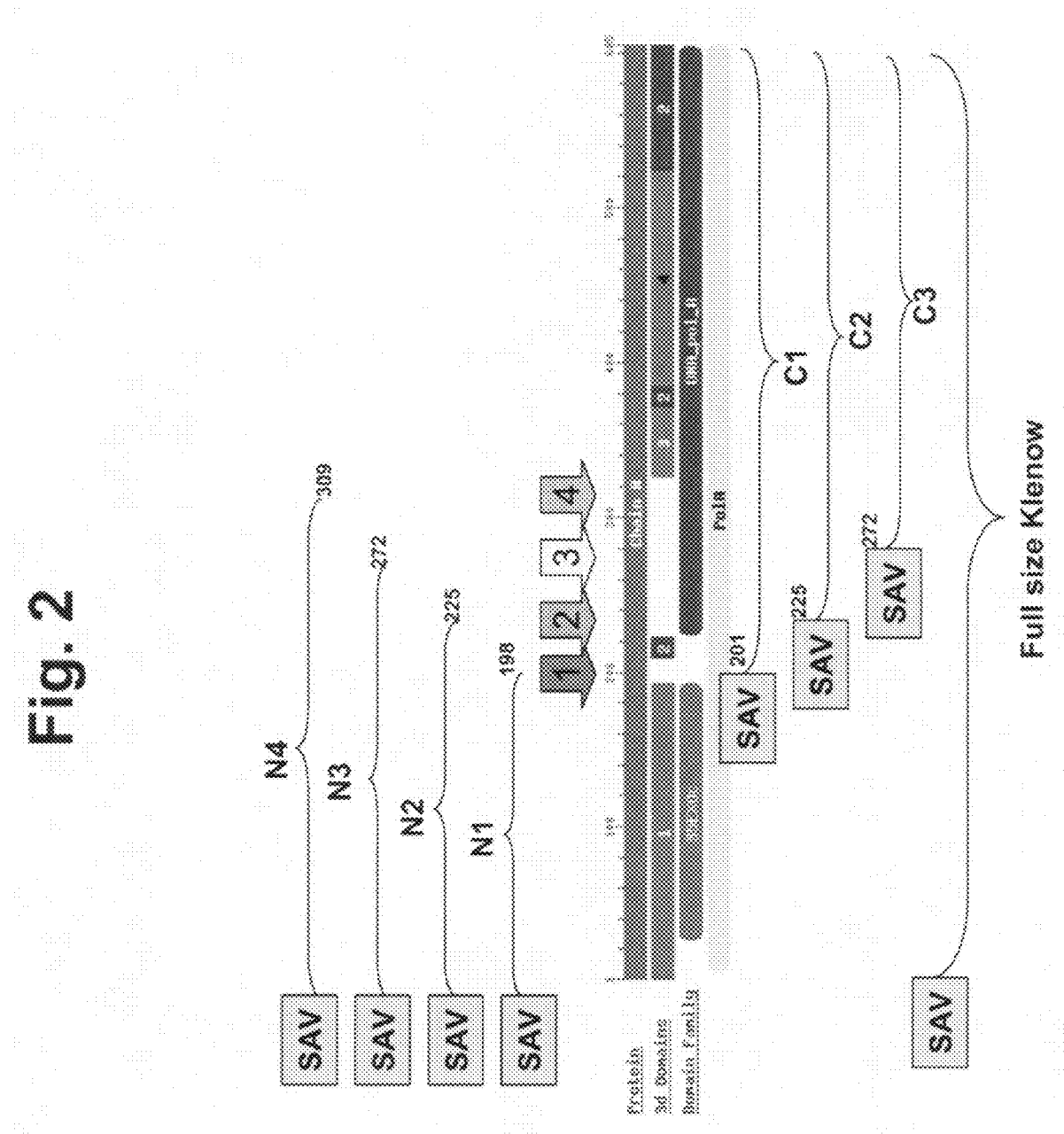
FIG. 2 illustrates the full-length klenow enzyme and various portions that may be useful in practicing the invention.

The following assay was performed for each of the N-terminal/C-terminal klenow split shown in FIG. 2 to identify the optimal constructs for use in practicing the present invention. Results and conditions for the N2/C2 split are described below.

Briefly, klenow N2 and C2 Streptavidin-fusion proteins (See FIG. 2) were diluted in 30 mM sodium phosphate pH 7.2, 50 mM NaCl, 4 mM DTT, 50% glycerol to concentrations of 0.19 mg/ml and 0.27 mg/ml respectively.

The following reaction mixtures were then prepared:
2 ul of each of klenow N2 and C2 fusion polypeptides
6 ul of reaction mixture containing 16 mM Tris-HCl pH 7.5, 8 mM MgCl2, 4 mM DTT, 0.5 mM DNTPs
0.2 mM Reverse primer:
5'-ACGAGGCTGCAATATCCAGA-3'
0.1 mM Oligo 1 template:
5'-TTTTTTTGCTCGACGGTGAAUGAUGTAG-GUACCAGC AGUAACUCGAGCACGUCUU 2'OMe(CG)A 2'OMe(CC) AAATCUGGAUATTG-CAGCCTCGT-3'
83 mer phosphodiester DNA/2'OMe; U indicates 2'deoxyuridine
25 ug/ml biotin labeled goat anti-rabbit IGG at 25 ug/ml concentration (American Quialex, San Clemente, Calif.).

The reaction mixtures were incubated at room temperature overnight allowing the split polymerase fusion polypeptides to bind the biotinylated antibody to form a functional klenow complex and copy the oligo 1 template so as to form an amplification product.

The next day the reaction mixtures were diluted 1:250 with water. 12.1 ul of each diluted reaction mixture was combined with 12.9 ul of a QPCR Master Mix. The QPCR amplification Master Mix included (all conc. are final after mixing with sample):
15 mM Tris-HCl pH 8.4
50 mM KCl
2.5 mM MgCl2
3% DMSO
0.01% Tween-20
800 nM dNTPs (ACGT)
0.444×SYBR Green (Molecular Probes, provided as 10,000×)
30 nM Rox reference dye (Stratagene Cat #600530)
Pfu(exo−) 50 U/ml (Stratagene Cat #600163-81)
100 nM Alien1-Forward primer:
5'-TGCTCGACGGTGAATGATGT-3
100 nM Alien1-Reverse primer:
5'-ACGAGGCTGCAATATCCAGA-3'

Samples were mixed and run in an MX3005P real-time PCR devise using the program for SYBR green with dissociation curve and 2-step cycling parameters of [95 C for 10 min] (1 cycle), [95 C for 15 sec, 63 C for 45 sec] (40 cycles).

Figure 3:
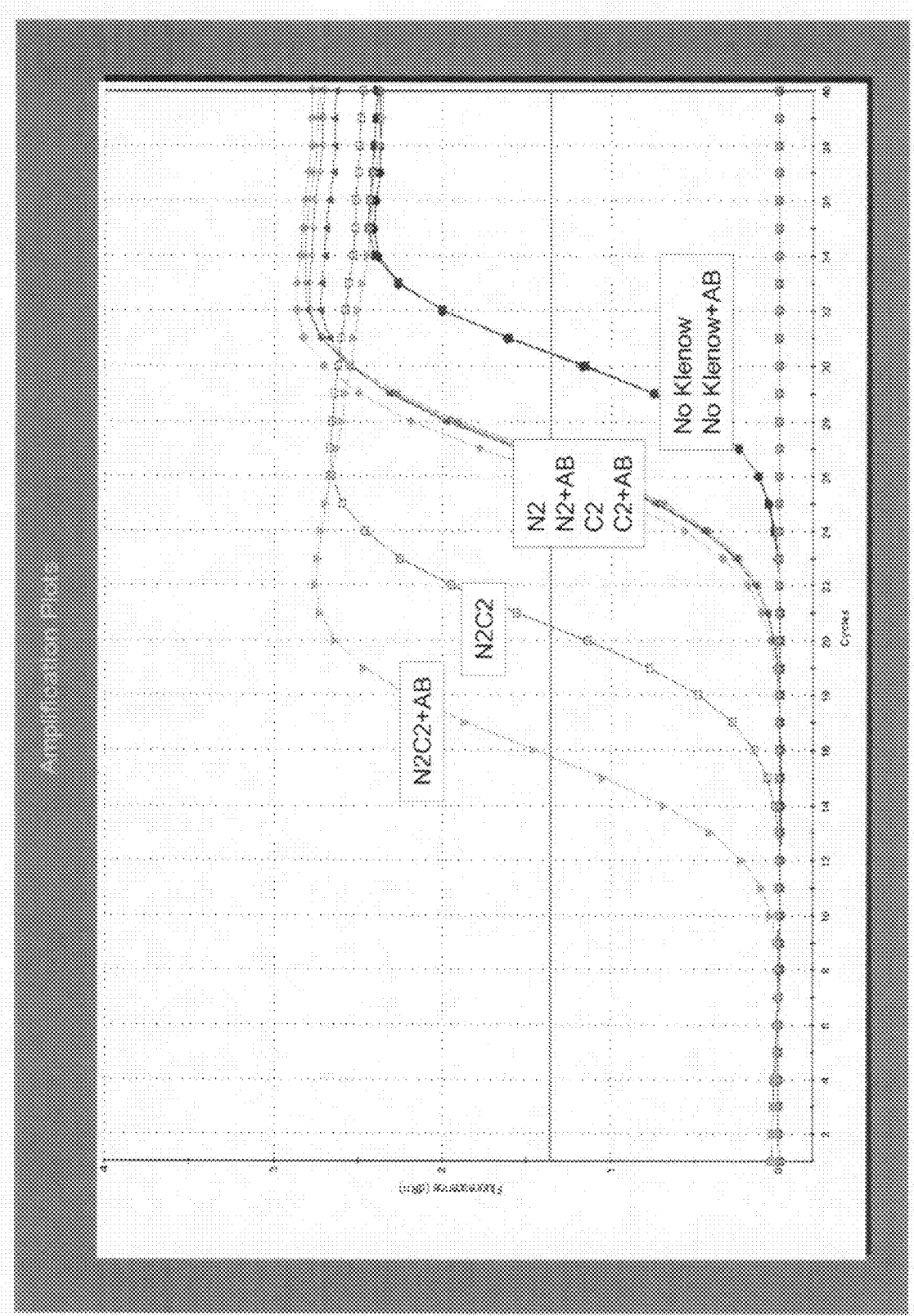
FIG. 3 depicts the results of a detection reaction utilizing the N2 and C2 fragments of klenow in the presence of biotinylated antibody.

The QPCR data is represented on FIG. 3. As expected, combination of both halves of split klenow with biotinylated antibodies (N2C2+AB) resulted in a substantially better signal than combination of both halves without the antibodies (N2C2). This indicates that proximity interaction between the two parts of split klenow is facilitated by their binding to the antibodies and interaction of the polymerase portions.

Example 2

Optimization of Working Range (Titration of Analyte)

In order to determine the optimal antibody concentration for use with the split klenow fusion polypeptides the reaction mixtures were prepared and processed as in Example 1, except that the concentration of split klenow portions, reverse primer and the template were 100× less, and the reactions were supplemented with 0.01% BSA (New England Biolabs, Beverly, Mass.).

To study the dose response, antibodies concentrations were varied from the 1 biotin molecules per 1 klenow molecule (1:1 ratio) of Example 1. Biotinylated antibody concentrations were adjusted to produce biotin-to-klenow ratios of 1:100, 1:10, 1:3.33, 1:1, 3.33:1, 10:1, and 100:1 were used.

QPCR data is shown in FIG. 4. The x-axis show the ratio of analyte (biotin)-to-klenow and the y-axis shows the 'Relative QPCR Signal'. As expected, the signal from binary binding rises as more analyte (biotinylated Ab) is added until it reaches a maximum at an approximate 1:10 ratio of biotin-to-klenow. Further addition of analyte past the equimolar ratio reduces the number of analytes that become bound by both halves simultaneously and the signal drops.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method for detecting an analyte in a sample, said method comprising:
    a. forming a reaction mixture comprising:
        a first analyte specific probe and a second analyte specific probe, wherein said first analyte specific probe comprises a first binding moiety and a first portion of a first polymerase and wherein said second analyte specific probe comprises a second binding moiety and a second portion of said first polymerase,
        a modified polynucleotide template,
        a first primer complementary to said polynucleotide template,
        a second polymerase, and
        a second primer complementary to an amplification template;
    b. incubating said reaction mixture so as to permit:
        said first and said second binding moieties to bind to said analyte such that said first and said second portions of said first polymerase interact to form a polymerase complex,
        annealing of said first primer to said modified polynucleotide template, and
        extending said primer by said polymerase complex thereby synthesizing said amplification template;
    c. annealing said second primer to said amplification template and extending said primer with said second polymerase and amplifying said amplification template with said second polymerase, wherein said second polymerase is unable to amplify the modified polynucleotide template under the conditions of the first primer extension reaction; and
    d. detecting said amplified amplification template wherein detection of said amplified amplification template is indicative of the presence or amount of said analyte in a sample.

2. A method for detecting an analyte in a sample, said method comprising:
    a. contacting a sample with a reaction mixture so as to permit:
        binding of a first analyte specific probe and a second analyte specific probe to an analyte so as to form a polymerase complex, wherein said first analyte specific probe comprises a first binding moiety and a first portion of a first polymerase and wherein said second analyte specific probe comprises a second binding moiety and a second portion of said first polymerase,
        annealing a first primer to a modified polynucleotide template, and
        extending said primer with said polymerase complex thereby synthesizing an amplification template;
    b. annealing a second primer to said amplification template and extending said second primer with a second polymerase and amplifying said amplification template with said second polymerase, wherein said second polymerase is unable to amplify the modified polynucleotide template under the conditions of the first primer extension reaction; and
    c. detecting said amplified amplification template, wherein detection of said amplified amplification template is indicative of the presence or amount of said analyte in a sample.

3. The method of claim 2, wherein said binding moiety is selected from the group consisting of a monoclonal antibody, polyclonal antibody, lectin, cell surface receptor, receptor ligand, peptide, carbohydrate, aptamer, biotin, streptavidin, avidin, protein A and protein G.

4. The method of claim 2, wherein said analyte is selected from the group consisting of a protein, oligonucleotide, cell surface receptor and receptor ligand.

5. The method of claim 2, wherein said detecting is performed during a real-time PCR reaction.

6. The method of claim 2, wherein said detecting comprises a nucleic acid cleavage reaction.

7. The method of claim 2, wherein said detecting further comprises a labeled probe that anneals downstream of said second primer.

8. The method of claim 2, wherein said first portion of said first polymerase comprises the amino acid sequence of SEQ ID NO:2 and said second portion of said first polymerase comprises the amino acid sequence of SEQ ID NO:3.

9. The method of claim 2, wherein said detecting comprises detecting an amplification product of the extended second primer.

10. The method of claim 2, wherein said second polymerase is Pfu DNA polymerase or hot start Taq DNA polymerase.

11. The method of claim 2, wherein said reaction mixture is treated with uracil deglycosylase prior to extending said second primer with said second polymerase.

12. The method of claim 1, wherein the first and second binding moieties are antibodies.

13. The method of claim 1, wherein the polymerase complex is Klenow or T4.

14. The method of claim 12, wherein the antibodies are coupled to the first and second portions of the first polymerase by a streptavidin-biotin interaction.

15. The method of claim 14, wherein the antibodies are biotinylated and the first and second portions of the first polymerase are coupled to streptavidin.

16. The method of claim 1, wherein the modified polynucleotide template comprises one or more deoxyuracils and/or one or more 2' O-methyl modifications.

17. The method of claim 2, wherein the first and second binding moieties are antibodies.

18. The method of claim 2, wherein the polymerase complex is Klenow or T4.

19. The method of claim 17, wherein the antibodies are coupled to the first and second portions of the first polymerase by a streptavidin-biotin interaction.

20. The method of claim 19, wherein the antibodies are biotinylated and the first and second portions of the first polymerase are coupled to streptavidin.

21. The method of claim 2, wherein the modified polynucleotide template comprises one or more deoxyuracils and/or one or more 2' O-methyl modifications.

* * * * *

SEQUENCE LISTING

<160> NUMBER OF SEQ ID NOS: 3

<210> SEQ ID NO 1
<211> LENGTH: 605
<212> TYPE: PRT
<213> ORGANISM: Escherichia coli

<400> SEQUENCE: 1

```
Val Ile Ser Tyr Asp Asn Tyr Val Thr Ile Leu Asp Glu Glu Thr Leu
1               5                   10                  15

Lys Ala Trp Ile Ala Lys Leu Glu Lys Ala Pro Val Phe Ala Phe Ala
                20                  25                  30

Thr Ala Thr Asp Ser Leu Asp Asn Ile Ser Ala Asn Leu Val Gly Leu
            35                  40                  45

Ser Phe Ala Ile Glu Pro Gly Val Ala Ala Tyr Ile Pro Val Ala His
        50                  55                  60

Asp Tyr Leu Asp Ala Pro Asp Gln Ile Ser Arg Glu Arg Ala Leu Glu
65                  70                  75                  80

Leu Leu Lys Pro Leu Leu Glu Asp Glu Lys Ala Leu Lys Val Gly Gln
                85                  90                  95

Asn Leu Lys Tyr Asp Arg Gly Ile Leu Ala Asn Tyr Gly Ile Glu Leu
            100                 105                 110

Arg Gly Ile Ala Phe Asp Thr Met Leu Glu Ser Tyr Ile Leu Asn Ser
        115                 120                 125

Val Ala Gly Arg His Asp Met Asp Ser Leu Ala Glu Arg Trp Leu Lys
    130                 135                 140

His Lys Thr Ile Thr Phe Glu Glu Ile Ala Gly Lys Gly Lys Asn Gln
145                 150                 155                 160

Leu Thr Phe Asn Gln Ile Ala Leu Glu Glu Ala Gly Arg Tyr Ala Ala
                165                 170                 175

Glu Asp Ala Asp Val Thr Leu Gln Leu His Leu Lys Met Trp Pro Asp
            180                 185                 190

Leu Gln Lys His Lys Gly Pro Leu Asn Val Phe Glu Asn Ile Glu Met
        195                 200                 205

Pro Leu Val Pro Val Leu Ser Arg Ile Glu Arg Asn Gly Val Lys Ile
    210                 215                 220

Asp Pro Lys Val Leu His Asn His Ser Glu Glu Leu Thr Leu Arg Leu
225                 230                 235                 240

Ala Glu Leu Glu Lys Lys Ala His Glu Ile Ala Gly Glu Glu Phe Asn
                245                 250                 255

Leu Ser Ser Thr Lys Gln Leu Gln Thr Ile Leu Phe Glu Lys Gln Gly
            260                 265                 270

Ile Lys Pro Leu Lys Lys Thr Pro Gly Gly Ala Pro Ser Thr Ser Glu
        275                 280                 285
```

```
Glu Val Leu Glu Glu Leu Ala Leu Asp Tyr Pro Leu Pro Lys Val Ile
    290                 295                 300

Leu Glu Tyr Arg Gly Leu Ala Lys Leu Lys Ser Thr Tyr Thr Asp Lys
305                 310                 315                 320

Leu Pro Leu Met Ile Asn Pro Lys Thr Gly Arg Val His Thr Ser Tyr
                325                 330                 335

His Gln Ala Val Thr Ala Thr Gly Arg Leu Ser Ser Thr Asp Pro Asn
            340                 345                 350

Leu Gln Asn Ile Pro Val Arg Asn Glu Glu Gly Arg Arg Ile Arg Gln
        355                 360                 365

Ala Phe Ile Ala Pro Glu Asp Tyr Val Ile Val Ser Ala Asp Tyr Ser
    370                 375                 380

Gln Ile Glu Leu Arg Ile Met Ala His Leu Ser Arg Asp Lys Gly Leu
385                 390                 395                 400

Leu Thr Ala Phe Ala Glu Gly Lys Asp Ile His Arg Ala Thr Ala Ala
                405                 410                 415

Glu Val Phe Gly Leu Pro Leu Glu Thr Val Thr Ser Glu Gln Arg Arg
            420                 425                 430

Ser Ala Lys Ala Ile Asn Phe Gly Leu Ile Tyr Gly Met Ser Ala Phe
        435                 440                 445

Gly Leu Ala Arg Gln Leu Asn Ile Pro Arg Lys Glu Ala Gln Lys Tyr
    450                 455                 460

Met Asp Leu Tyr Phe Glu Arg Tyr Pro Gly Val Leu Glu Tyr Met Glu
465                 470                 475                 480

Arg Thr Arg Ala Gln Ala Lys Glu Gln Gly Tyr Val Glu Thr Leu Asp
                485                 490                 495

Gly Arg Arg Leu Tyr Leu Pro Asp Ile Lys Ser Ser Asn Gly Ala Arg
            500                 505                 510

Arg Ala Ala Ala Glu Arg Ala Ala Ile Asn Ala Pro Met Gln Gly Thr
        515                 520                 525

Ala Ala Asp Ile Ile Lys Arg Ala Met Ile Ala Val Asp Ala Trp Leu
    530                 535                 540

Gln Ala Glu Gln Pro Arg Val Arg Met Ile Met Gln Val His Asp Glu
545                 550                 555                 560

Leu Val Phe Glu Val His Lys Asp Asp Val Asp Ala Val Ala Lys Gln
                565                 570                 575

Ile His Gln Leu Met Glu Asn Cys Thr Arg Leu Asp Val Pro Leu Leu
            580                 585                 590

Val Glu Val Gly Ser Gly Glu Asn Trp Asp Gln Ala His
        595                 600                 605

<210> SEQ ID NO 2
<211> LENGTH: 225
<212> TYPE: PRT
<213> ORGANISM: Escherichia coli

<400> SEQUENCE: 2

Val Ile Ser Tyr Asp Asn Tyr Val Thr Ile Leu Asp Glu Glu Thr Leu
1               5                   10                  15

Lys Ala Trp Ile Ala Lys Leu Glu Lys Ala Pro Val Phe Ala Phe Ala
                20                  25                  30

Thr Ala Thr Asp Ser Leu Asp Asn Ile Ser Ala Asn Leu Val Gly Leu
            35                  40                  45

Ser Phe Ala Ile Glu Pro Gly Val Ala Ala Tyr Ile Pro Val Ala His
```

```
            50                  55                  60
Asp Tyr Leu Asp Ala Pro Asp Gln Ile Ser Arg Glu Arg Ala Leu Glu
65                  70                  75                  80

Leu Leu Lys Pro Leu Leu Glu Asp Glu Lys Ala Leu Lys Val Gly Gln
                85                  90                  95

Asn Leu Lys Tyr Asp Arg Gly Ile Leu Ala Asn Tyr Gly Ile Glu Leu
            100                 105                 110

Arg Gly Ile Ala Phe Asp Thr Met Leu Glu Ser Tyr Ile Leu Asn Ser
        115                 120                 125

Val Ala Gly Arg His Asp Met Asp Ser Leu Ala Glu Arg Trp Leu Lys
130                 135                 140

His Lys Thr Ile Thr Phe Glu Glu Ile Ala Gly Lys Gly Lys Asn Gln
145                 150                 155                 160

Leu Thr Phe Asn Gln Ile Ala Leu Glu Glu Ala Gly Arg Tyr Ala Ala
                165                 170                 175

Glu Asp Ala Asp Val Thr Leu Gln Leu His Leu Lys Met Trp Pro Asp
            180                 185                 190

Leu Gln Lys His Lys Gly Pro Leu Asn Val Phe Glu Asn Ile Glu Met
        195                 200                 205

Pro Leu Val Pro Val Leu Ser Arg Ile Glu Arg Asn Gly Val Lys Ile
    210                 215                 220

Asp
225

<210> SEQ ID NO 3
<211> LENGTH: 381
<212> TYPE: PRT
<213> ORGANISM: Escherichia coli

<400> SEQUENCE: 3

Asp Pro Lys Val Leu His Asn His Ser Glu Glu Leu Thr Leu Arg Leu
1               5                   10                  15

Ala Glu Leu Glu Lys Lys Ala His Glu Ile Ala Gly Glu Glu Phe Asn
            20                  25                  30

Leu Ser Ser Thr Lys Gln Leu Gln Thr Ile Leu Phe Glu Lys Gln Gly
        35                  40                  45

Ile Lys Pro Leu Lys Lys Thr Pro Gly Gly Ala Pro Ser Thr Ser Glu
    50                  55                  60

Glu Val Leu Glu Glu Leu Ala Leu Asp Tyr Pro Leu Pro Lys Val Ile
65                  70                  75                  80

Leu Glu Tyr Arg Gly Leu Ala Lys Leu Lys Ser Thr Tyr Thr Asp Lys
                85                  90                  95

Leu Pro Leu Met Ile Asn Pro Lys Thr Gly Arg Val His Thr Ser Tyr
            100                 105                 110

His Gln Ala Val Thr Ala Thr Gly Arg Leu Ser Ser Thr Asp Pro Asn
        115                 120                 125

Leu Gln Asn Ile Pro Val Arg Asn Glu Glu Gly Arg Arg Ile Arg Gln
    130                 135                 140

Ala Phe Ile Ala Pro Glu Asp Tyr Val Ile Val Ser Ala Asp Tyr Ser
145                 150                 155                 160

Gln Ile Glu Leu Arg Ile Met Ala His Leu Ser Arg Asp Lys Gly Leu
                165                 170                 175

Leu Thr Ala Phe Ala Glu Gly Lys Asp Ile His Arg Ala Thr Ala Ala
            180                 185                 190
```

-continued

```
Glu Val Phe Gly Leu Pro Leu Glu Thr Val Thr Ser Glu Gln Arg Arg
            195                 200                 205

Ser Ala Lys Ala Ile Asn Phe Gly Leu Ile Tyr Gly Met Ser Ala Phe
    210                 215                 220

Gly Leu Ala Arg Gln Leu Asn Ile Pro Arg Lys Glu Ala Gln Lys Tyr
225                 230                 235                 240

Met Asp Leu Tyr Phe Glu Arg Tyr Pro Gly Val Leu Glu Tyr Met Glu
                245                 250                 255

Arg Thr Arg Ala Gln Ala Lys Glu Gln Gly Tyr Val Glu Thr Leu Asp
                260                 265                 270

Gly Arg Arg Leu Tyr Leu Pro Asp Ile Lys Ser Ser Asn Gly Ala Arg
        275                 280                 285

Arg Ala Ala Ala Glu Arg Ala Ala Ile Asn Ala Pro Met Gln Gly Thr
    290                 295                 300

Ala Ala Asp Ile Ile Lys Arg Ala Met Ile Ala Val Asp Ala Trp Leu
305                 310                 315                 320

Gln Ala Glu Gln Pro Arg Val Arg Met Ile Met Gln Val His Asp Glu
                325                 330                 335

Leu Val Phe Glu Val His Lys Asp Asp Val Asp Ala Val Ala Lys Gln
                340                 345                 350

Ile His Gln Leu Met Glu Asn Cys Thr Arg Leu Asp Val Pro Leu Leu
        355                 360                 365

Val Glu Val Gly Ser Gly Glu Asn Trp Asp Gln Ala His
    370                 375                 380
```